(12) United States Patent
Wich et al.

(10) Patent No.: US 6,180,373 B1
(45) Date of Patent: Jan. 30, 2001

(54) MICROORGANISMS FOR THE PRODUCTION OF TRYPTOPHAN AND PROCESS FOR THE PREPARATION THEREOF

(75) Inventors: Günter Wich; Walfred Leinfelder, both of Müchen (DE); Keith Backman, Bedford, MA (US)

(73) Assignee: Consortium für elektrochemische Industrie GmbH, Munich (DE)

( * ) Notice: Under 35 U.S.C. 154(b), the term of this patent shall be extended for 0 days.

(21) Appl. No.: 08/411,760

(22) PCT Filed: Sep. 23, 1993

(86) PCT No.: PCT/EP93/02588

§ 371 Date: Apr. 12, 1995

§ 102(e) Date: Apr. 12, 1995

(87) PCT Pub. No.: WO94/08031

PCT Pub. Date: Apr. 14, 1994

(30) Foreign Application Priority Data

Sep. 28, 1992 (DE) ................................ 42 32 468

(51) Int. Cl.⁷ .............................. C12P 13/22; C12N 1/20; C12N 1/21; C12N 15/00

(52) U.S. Cl. ............... 435/108; 435/252.32; 435/252.33; 435/252.8; 435/252.1; 435/440; 435/477; 435/487; 435/843; 435/849

(58) Field of Search ................................ 435/108, 172.3, 435/252.3, 252.33, 252.8, 320.1, 252.32, 252.1, 440, 477, 487, 488, 843, 849; 935/27, 28, 29, 52, 55, 56, 60, 73

(56) References Cited

U.S. PATENT DOCUMENTS

| | | |
|---|---|---|
| 3,385,762 | 5/1968 | Okazaki . |
| 3,594,279 | 7/1971 | Nakayama et al. . |
| 3,849,251 | 11/1974 | Nakayama et al. . |
| 4,363,875 | 12/1982 | Akashiba et al. . |
| 4,371,614 * | 2/1983 | Anderson et al. .................. 435/108 |
| 4,588,687 | 5/1986 | Tsuchida et al. . |
| 4,965,191 | 10/1990 | Liebl et al. . |
| 5,618,716 * | 4/1997 | Burlingame ........................ 435/106 |

FOREIGN PATENT DOCUMENTS

| | | |
|---|---|---|
| 1182409 | 2/1985 | (CA) . |
| 3123001 | 7/1982 | (DE) . |
| 0149539 | 7/1985 | (EP) . |
| 0293207 | 11/1988 | (EP) . |
| 0338474 | 10/1989 | (EP) . |
| 0401735 | 12/1990 | (EP) . |
| 0488424 | 3/1992 | (EP) . |
| 87/01130 * | 2/1987 | (WO) ............................ C12N/15/00 |
| 93/12235 * | 6/1993 | (WO) ............................ C12N/15/53 |

OTHER PUBLICATIONS

Somerville, R.L., Herrmann, K.M., 1983, Aminoacids, Biosynthesis and Genetic Regulation, Adelison–Wesley Publishing Company, USA: 301–322 and 351–378.

Aida et al., 1986, Biotechnology of amino acid production, progress in industrial microbiology vol. 24, Elsevier Science Publishers, Amsterdam: 188–206.

Tosa T., Pizer L.J., 1971, Journal of Bacteriology vol. 106, No. 3, 972–982; "Biochemical Bases for the Antimetabolite Action of L–Serine Hydroxamate".

Winicov I., Pizer L.J., 1974, Journal of Biological Chemistry vol. 249: 1348–1355, "The Mechanism of End Product Inhibition of Serine Biosynthesis".

Miller J.H., 1972, Experiments in Molecular Genetics, Cold Spring Harbor Laboratory, USA: 113–185 Introduction to Unit III.

Bauerle R. et al., 1987, Methods in Enzymology, vol. 142: 366–386 "Anthranilate Synthase–Anthranilate Phosphoribosyltransferase Complex and Subunits of *Salmonella typhimurium*".

Caliqiuiri M.G., Bauerle R., 1991, J. of Biol. Chem. vol. 266: No. 13; pp. 8328–8335; "Indentification of Amino Acid Residues Involved in Feedback Regulation of the Anthranilate Synthase Complex from *Salomonella typhimurium*".

Matsui K. et al., 1987, J. Bact. vol. 169: 5330–5332; "Two Single–Base–Pair Substitutions Causing Desensitization to Tryptophan Feedback Inhibition of Anthranilate Synthase and Enhanced Expression of Tryptophan Genes of *Brevibacterium lactofermentum*".

Sarkar G., Sommer, S.S., 1990, Bio Techniques 8: 404–407 "The "Megaprimer" Method of Site–Directed Mutagenesis".

Ausubel F.M. et al., 1987, Current Protocols in Molecular Biology, Greene Publishing Associates, "Mutagenesis of Cloned DNA".

Smith M., 1985, Ann. Rev., Genet., 19: 423–462, "In Vitro Mutagenesis".

Morse D.E., Yanofsky C., J. Mol. Biol. 44, 1969, 185–193; "Amber Mutants of the trp Regulatory Gene".

Junetsu Ito and Irving P. Crawford; Genetics 52, 1965, 1303–1316, "Regulation of the Enzymes of the Tryptophan Pathway in *Escherichia coli*".

(List continued on next page.)

Primary Examiner—Mary E. Mosher
(74) Attorney, Agent, or Firm—Collard & Roe, P.C.

(57) ABSTRACT

A tryptophan producing strain of microorganism is selected from *E. coli* and Corynebacteria and is tryptophan feedback resistant and serine feedback resistant. The serine feedback resistance is by a mutation in a serA allele, where the mutated serA allele codes for a protein which has a $K_i$ value for serine between 0.1 mM and 50 mM. The tryptophan feedback resistance is by a trpE allele which codes for a protein which has a $K_i$ value for tryptophan between 0.1 mM and 20 mM. A process for preparing this microorganism and a process for using this microorganism are disclosed.

10 Claims, 10 Drawing Sheets

OTHER PUBLICATIONS

Theodore K. Gartner and Monica Riley; J. Bact. 89, No. 2, 1965, 313–318 (erroneously cited as: J. Bact. 85, 1965, 680–685) "Isolation of Mutants Affecting Tryptophanase Production in *Escherichia coli*".

Karen L. Tobey and Gregory A. Grant, 1986, J. Biol. Chem. vol. 261, No. 26, pp. 12179–12183 "The Nucleotide Sequence of the serA Gene of *Escherichia coli* and the Amino Acid Sequence of the Encoded Protein, D–3–Phosphoglycerate Dehydrogenase".

Schuller et al., 1989, J. Biol. Chem. vol. 264: 2645–2648; "Enhanced Expression of the *Escherichia coli* serA Gene in a Plasmid".

Maniatis T., Fritsch E.F., und Sambrook J., Molecular Cloning; A Laboratory Manual 1982, Cold Spring Harbor Laboratory, 4 "Enzymes Used in Molecular Cloning".

Mc Kitrick, J.C. and Pizer, L.I., 1980, J. Bact. 141: 235–245, "Regulation of Phosphoglycerate Dehydrogenase Levels and Effect on Serine Synthesis in *Escherichia coli* K–12".

Pouwels P.H., Enger–Valk B.E., Brammar W.J., 1985, Cloning Vectors, Elsevier, Amsterdam, "A Laboratory Manual".

Ausubel F.M., et al., 1987, Current Protocols in Molecular Biology, Greene Publishing Associates, USA; "Construction of Recombinant DNA Libraries".

Ramaswamy Balakrishnan and Keith Backman, 1988, Gene, 67: 97–103 Elsevier, "Controllable alteration of cell genotype in bacterial cultures using an excision vector".

Simons R.W. et al., 1987, Gene, 53: 85–89, Elsevier, "Improved single and multicopy lac–based cloning vectors for protein and operon fusions".

Shevell et al., 1988, J. Bact. 170, No. 7, p. 3294–3296, (erroneously cited as: Shervell et al., 1987, J. bact. 141: 235–245), "Construction of an *Escherichia coli* K–12 ada Deletion by Gene Replacement in a recD Strain reveals a second Methyltransferase that repairs alkylated DNA".

Thomas J. Silhavy et al., 1984, Experiments with Gene Fusions, Cold Spring Harbor Laboratory.

Miller J.H., 1972, Experiments in Molecular Genetics, Cold Spring Harbor Laboratory, Cold Spring Harbor, N.Y.: 125–129, Experiment 14, "Nitrosguanidine Mutagenesis".

Cohen et al., 1972, Proc. Natl. Acad. Sci. USA 69: 2110–2114, "Nonchromosomal Antibiotic Resistance in Bacteria: Genetic Transformation of *Escherichia coli* by R–Factor DNA".

Miller J.H., 1972, Experiments in Molecular Genetics, Cold Spring Harbor, N.Y.: 201–205, "Generalized Transduction; Use of P1 in Strain Construction".

Ausubel et al., 1987, 2.4.1–2.4.2, Current Protocols in Molecular Biology, Greene Publishing Associates, "Preparation of Genomic DNA from Bacteria".

Maniatis et al., 1982, Molecular Cloning: A Laboratory Manual, Cold Spring Harbor Laboratory, Cold Spring Harbor, N.Y.: 396–397, "Attachment of Synthetic Linkers".

Hendrik Wolf et al., 1989, Appl. Microbiol. Biotechnol. 30: 283–289, "Electrotransformation of intact and osmotically sensitive cells of Corynebacterium glutamicum".

CA 111:168688q.

CA 111:168689r.

J. Mandelstam et al. Biochemistry of Bacterial Growth, 3rd Edition, John Wiley & Sons, New York, pp. 159–183, 1982.*

* cited by examiner

Fig. 3a

```
              10                    30                    50
               .                     .                     .
ATGGCAAAGGTATCGCTGGAGAAAGACAAGATTAAGTTTCTGCTGGTAGAAGGCGTGCAC
MetAlaLysValSerLeuGluLysAspLysIleLysPheLeuLeuValGluGlyValHis 70                    90                   110
               .                     .                     .
CAAAAGGCGCTGGAAAGCCTTCGTGCAGCTGGTTACACCAACATCGAATTTCACAAAGGC
GlnLysAlaLeuGluSerLeuArgAlaAlaGlyTyrThrAsnIleGluPheHisLysGly 130                   150                   170
               .                     .                     .
GCGCTGGATGATGAACAATTAAAAGAATCCATCCGCGATGCCCACTTCATCGGCCTGCGA
AlaLeuAspAspGluGlnLeuLysGluSerIleArgAspAlaHisPheIleGlyLeuArg 190                   210                   230
               .                     .                     .
TCCCGTACCCATCTGACTGAAGACGTGATCAACGCCGCAGAAAAACTGGTCGCTATTGGC
SerArgThrHisLeuThrGluAspValIleAsnAlaAlaGluLysLeuValAlaIleGly 250                   270                   290
               .                     .                     .
TGTTTCTGTATCGGAACAAACCAGGTTGATCTGGATGCGGCGGCAAAGCGCGGGATCCCG
CysPheCysIleGlyThrAsnGlnValAspLeuAspAlaAlaAlaLysArgGlyIlePro 310                   330                   350
               .                     .                     .
GTATTTAACGCACCGTTCTCAAATACGCGCTCTGTTGCGGAGCTGGTGATTGGCGAACTG
ValPheAsnAlaProPheSerAsnThrArgSerValAlaGluLeuValIleGlyGluLeu 370                   390                   410
               .                     .                     .
CTGCTGCTATTGCGCGGCGTGCCGGAAGCCAATGCTAAAGCGCACCGTGGCGTGTGGAAC
LeuLeuLeuLeuArgGlyValProGluAlaAsnAlaLysAlaHisArgGlyValTrpAsn
```

Fig. 3b

```
           430                 450                 470
            .                   .                   .
AAACTGGCGGCGGGTTCTTTTGAAGCGCGCGGCAAAAAGCTGGGTATCATCGGCTACGGT
LysLeuAlaAlaGlySerPheGluAlaArgGlyLysLysLeuGlyIleIleGlyTyrGly 490                 510                 530
            .                   .                   .
CATATTGGTACGCAATTGGGCATTCTGGCTGAATCGCTGGGAATGTATGTTTACTTTTAT
HisIleGlyThrGlnLeuGlyIleLeuAlaGluSerLeuGlyMetTyrValTyrPheTyr 550                 570                 590
            .                   .                   .
GATATTGAAAATAAACTGCCGCTGGGCAACGCCACTCAGGTACAGCATCTTTCTGACCTG
AspIleGluAsnLysLeuProLeuGlyAsnAlaThrGlnValGlnHisLeuSerAspLeu 610                 630                 650
            .                   .                   .
CTGAATATGAGCGATGTGGTGAGTCTGCATGTACCAGAGAATCCGTCCACCAAAAATATG
LeuAsnMetSerAspValValSerLeuHisValProGluAsnProSerThrLysAsnMet 670                 690                 710
            .                   .                   .
ATGGGCGCGAAAGAAATTTCACTAATGAAGCCCGGCTCGCTGCTGATTAATGCTTCGCGC
MetGlyAlaLysGluIleSerLeuMetLysProGlySerLeuLeuIleAsnAlaSerArg 730                 750                 770
            .                   .                   .
GGTACTGTGGTGGATATTCCGGCGCTGTGTGATGCGCTGGCGAGCAAACATCTGGCGGGG
GlyThrValValAspIleProAlaLeuCysAspAlaLeuAlaSerLysHisLeuAlaGly 790                 810                 830
            .                   .                   .
GCGGCAATCGACGTATTCCCGACGGAACCGGCGACCAATAGCGATCCATTTACCTCTCCG
AlaAlaIleAspValPheProThrGluProAlaThrAsnSerAspProPheThrSerPro
```

Fig. 3c

```
        850                 870                 890
         .                   .                   .
CTGTGTGAATTCGACAACGTCCTTCTGACGCCACACATTGGCGGTTCGACTCAGGAAGCG
LeuCysGluPheAspAsnValLeuLeuThrProHisIleGlyGlySerThrGlnGluAla 910                 930                 950
         .                   .                   .
CAGGAGAATATCGGCCTGGAAGTTGCGGGTAAATTGATCAAGTATTCTGACAATGGCTCA
GlnGluAsnIleGlyLeuGluValAlaGlyLysLeuIleLysTyrSerAspAsnGlySer 970                 990                1010
         .                   .                   .
ACGCTCTCTGCGGTGAACTTCCCGGAAGTCTCGCTGCCACTGCACGGTGGGCGTCGTCTG
ThrLeuSerAlaValAsnPheProGluValSerLeuProLeuHisGlyGlyArgArgLeu 1030                1050                1070
         .                   .                   .
ATGCACATCCACGAAAACCGTCCGGGCGTGCTAACTGCGCTGAACAAAATCTTCGCCGAG
MetHisIleHisGluAsnArgProGlyValLeuThrAlaLeuAsnLysIlePheAlaGlu 1090                1110                1130
         .                   .                   .
CAGGGCGTCAACATCGCCGCGCAATATCTGCAAACTTCCGCCCAGATGGGTTATGTGGTT
GlnGlyValAsnIleAlaAlaGlnTyrLeuGlnThrSerAlaGlnMetGlyTyrValVal 1150                1170                1190
         .                   .                   .
ATTGATATTGAAGCCGACGAAGACGTTGCCGAAAAAGCGCTGCAGGCAATGAAAGCTATT
IleAspIleGluAlaAspGluAspValAlaGluLysAlaLeuGlnAlaMetLysAlaIle 1210                1230
         .                   .
CCGGGTACCATTCGCGCCCGTCTGCTGTACTAA
ProGlyThrIleArgAlaArgLeuLeuTyrEnd
```

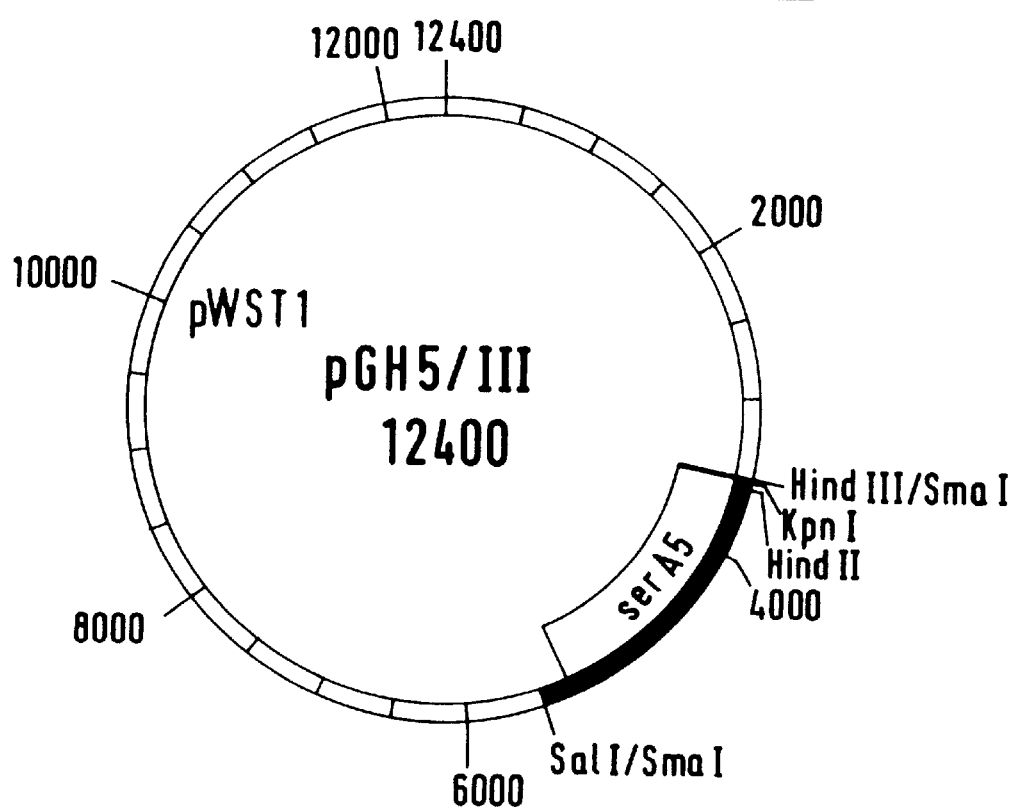
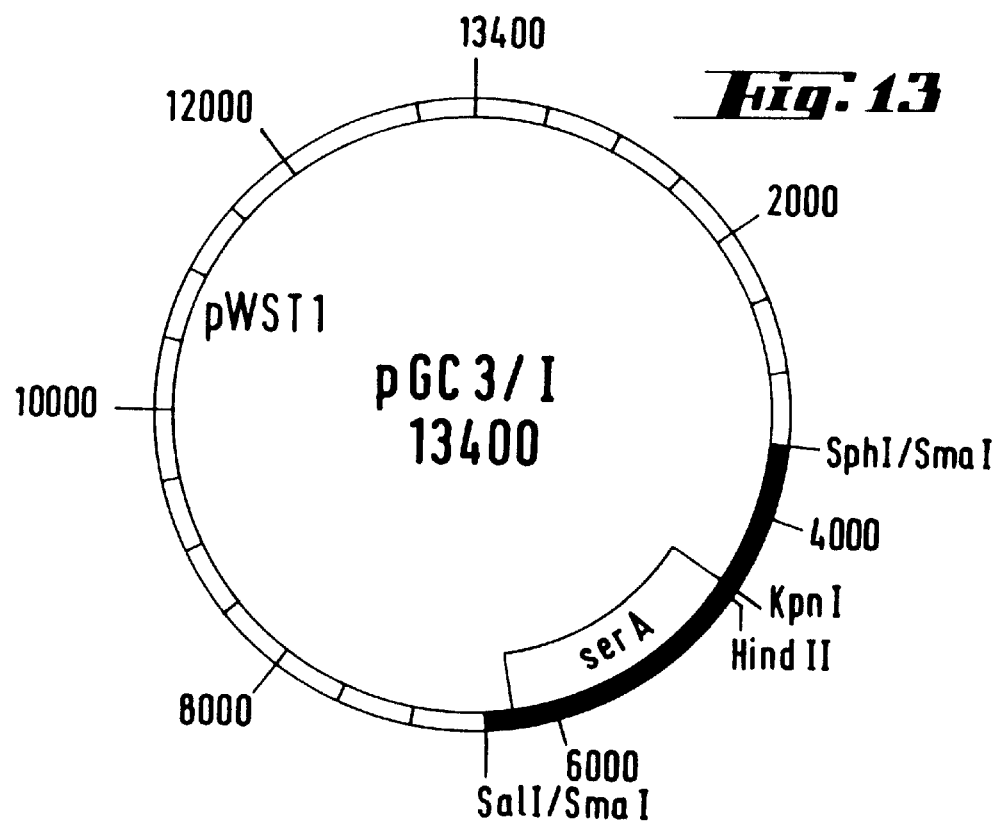

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 52 amino acids
      (B) TYPE: Amino acid
      (C) STRANDEDNESS: single
      (D) TOPOLOGY: linear (ii) MOLECULE TYPE: protein (iii) HYPOTHETICAL: YES (v) FRAGMENT TYPE: terminal fragment (vi) ORIGINAL SOURCE:
           (A) ORGANISM: Escherichia coli
           (B) STRAIN: B (vii) IMMEDIATE SOURCE:
           (B) CLONE: pGC3

(xi) SEQUENCE DESCRIPTION: SEQ ID NO:1:

Ala Glu Gln Gly Val Asn Ile Ala Ala Gln Tyr Leu Gln Thr Ser Ala
1               5                  10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg Ala
        35                  40                  45

Arg Leu Leu Tyr
    50

(2) INFORMATION FOR SEQ ID NO:2:

(i) SEQUENCE CHARACTERISTICS:
          (A) LENGTH: 51 amino acids
          (B) TYPE:    Amino acid
          (C) STRANDEDNESS: single
          (D) TOPOLOGY:  linear (ii) MOLECULE TYPE: protein (iii) HYPOTHETICAL: YES (v) FRAGMENT TYPE: C terminal fragment (vi) ORIGINAL SOURCE:
          (A) ORGANISM: Escherichia coli
          (B) STRAIN: B (vii) IMMEDIATE SOURCE:
          (B) CLONE: pGH5

(xi) SEQUENCE DESCRIPTION: SEQ ID NO:2:

Ala Glu Gln Gly Val Asn Ile Ala Ala Gln Tyr Leu Gln Thr Ser Ala
1               5                  10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg Ala
        35                  40                  45

Arg Leu Leu
    50

(2) INFORMATION FOR SEQ ID NO:3:

(i) SEQUENCE CHARACTERISTICS:
          (A) LENGTH: 56 amino acids
          (B) TYPE:    Amino acid
          (C) STRANDEDNESS: single
          (D) TOPOLOGY:  linear (ii) MOLECULE TYPE: protein (iii) HYPOTHETICAL: YES (v) FRAGMENT TYPE: C terminal fragment (vi) ORIGINAL SOURCE:
          (A) ORGANISM: Escherichia coli
          (B) STRAIN: B (vii) IMMEDIATE SOURCE:

(B) CLONE: pKB1508

(xi) SEQUENCE DESCRIPTION: SEQ ID NO:3:

Ala Glu Gln Gly Val Cys Ser Arg Ala Asn Ile Ala Ala Gln Tyr Leu
1               5                   10                  15

Gln Thr Ser Ala Gln Met Gly Tyr Val Val Ile Asp Ile Glu Ala Asp
                20                  25                  30

Glu Asp Val Ala Glu Lys Ala Leu Gln Ala Met Lys Ala Ile Pro Gly
            35                  40                  45

Thr Ile Arg Ala Arg Leu Leu Tyr
    50                  55

(2) INFORMATION FOR SEQ ID NO:4:

(i) SEQUENCE CHARACTERISTICS:
        (A) LENGTH: 55 amino acids
        (B) TYPE:   Amino acid
        (C) STRANDEDNESS: single
        (D) TOPOLOGY: linear (ii) MOLECULE TYPE: protein (iii) HYPOTHETICAL: YES (v) FRAGMENT TYPE: C terminal fragment (vi) ORIGINAL SOURCE:
        (A) ORGANISM: Escherichia coli
        (B) STRAIN:  B (vii) IMMEDIATE SOURCE:
        (B) CLONE: pGH11

(xi) SEQUENCE DESCRIPTION: SEQ ID NO:4:

Ala Glu Gln Gly Val Cys Ser Arg Ala Asn Ile Ala Ala Gln Tyr Leu
1               5                   10                  15

Gln Thr Ser Ala Gln Met Gly Tyr Val Val Ile Asp Ile Glu Ala Asp
                20                  25                  30

Glu Asp Val Ala Glu Lys Ala Leu Gln Ala Met Lys Ala Ile Pro Gly
            35                  40                  45

Thr Ile Arg Ala Arg Leu Leu
    50                  55

(2) INFORMATION FOR SEQ ID NO:5:

(i) SEQUENCE CHARACTERISTICS:
        (A) LENGTH: 47 amino acids
        (B) TYPE:   Amino acid
        (C) STRANDEDNESS: single
        (D) TOPOLOGY: linear (ii) MOLECULE TYPE: protein (iii) HYPOTHETICAL: YES (v) FRAGMENT TYPE: C terminal fragment (vi) ORIGINAL SOURCE:
        (A) ORGANISM: Escherichia coli
        (B) STRAIN:  B (vii) IMMEDIATE SOURCE:
        (B) CLONE: pKB1455

(xi) SEQUENCE DESCRIPTION: SEQ ID NO:5:

Ala Glu Gln Gly Val Asn Ile Ala Ala Gln Tyr Leu Gln Thr Ser Ala
1               5                   10                  15

```
Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg
        35                  40                  45

(2) INFORMATION FOR SEQ ID NO:6:

(i) SEQUENCE CHARACTERISTICS:
        (A) LENGTH:  32 amino acids
        (B) TYPE:    Amino acid
        (C) STRANDEDNESS:  single
        (D) TOPOLOGY:  linear (ii) MOLECULE TYPE:  protein (iii) HYPOTHETICAL:  YES (v) FRAGMENT TYPE: internal fragment (vi) ORIGINAL SOURCE:
        (A) ORGANISM:  Escherichia coli
        (B) STRAIN: YMC9

(xi) SEQUENCE DESCRIPTION:  SEQ ID NO:6:

Asn Pro Thr Ala Leu Phe His Gln Leu Cys Gly Asp Arg Pro Ala Thr
1               5                   10                  15

Leu Leu Leu Glu Ser Ala Asp Ile Asp Ser Lys Asp Asp Leu Lys Ser
            20                  25                  30

(2) INFORMATION FOR SEQ ID NO:7:

(i) SEQUENCE CHARACTERISTICS:
        (A) LENGTH:  32 amino acids
        (B) TYPE:    Amino acid
        (C) STRANDEDNESS:  single
        (D) TOPOLOGY:  linear (ii) MOLECULE TYPE:  protein (iii) HYPOTHETICAL:  YES (iii) ANTI-SENSE:    NO (v) FRAGMENT TYPE: internal fragment (vi) ORIGINAL SOURCE:
        (A) ORGANISM:  Escherichia coli
        (B) STRAIN: PD103

(xi) SEQUENCE DESCRIPTION:  SEQ ID NO:7:

Asn Pro Thr Ala Leu Phe His Gln Leu Cys Gly Asp Arg Pro Ala Thr
1               5                   10                  15

Leu Leu Leu Glu Ser Ala Asp Ile Asp Ser Lys Asp Asp Leu Glu Ser
            20                  25                  30

(2) INFORMATION FOR SEQ ID NO:8:

(i) SEQUENCE CHARACTERISTICS:
        (A) LENGTH:  32 amino acids
        (B) TYPE:    Amino acid
        (C) STRANDEDNESS:  single
        (D) TOPOLOGY:  linear (ii) MOLECULE TYPE:  protein (iii) HYPOTHETICAL:  YES (v) FRAGMENT TYPE: internal fragment (vi) ORIGINAL SOURCE:
        (A) ORGANISM:  Escherichia coli
```

(B) STRAIN: KB862

(xi) SEQUENCE DESCRIPTION: SEQ ID NO:8:

Asn Ser Thr Ala Leu Phe His Gln Leu Cys Gly Asp Arg Pro Ala Thr
1               5                   10                  15

Leu Leu Leu Glu Ser Ala Asp Ile Asp Ser Lys Asp Asp Leu Lys Ser
                20                  25                  30

(2) INFORMATION FOR SEQ ID NO:9:

(i) SEQUENCE CHARACTERISTICS:
        (A) LENGTH: 32 amino acids
        (B) TYPE: Amino acid
        (C) STRANDEDNESS: single
        (D) TOPOLOGY: linear (ii) MOLECULE TYPE: protein (iii) HYPOTHETICAL: YES (v) FRAGMENT TYPE: internal fragment (vi) ORIGINAL SOURCE:
        (A) ORGANISM: Escherichia coli
        (B) STRAIN: SV163

(xi) SEQUENCE DESCRIPTION: SEQ ID NO:9:

Asn Pro Thr Ala Leu Phe His Gln Leu Cys Gly Asp Arg Pro Ala Thr
1               5                   10                  15

Leu Leu Leu Glu Phe Ala Asp Ile Asp Ser Lys Asp Asp Leu Glu Ser
                20                  25                  30

(2) INFORMATION FOR SEQ ID NO:10:

(i) SEQUENCE CHARACTERISTICS:
        (A) LENGTH: 32 amino acids
        (B) TYPE: Amino acid
        (C) STRANDEDNESS: single
        (D) TOPOLOGY: linear (ii) MOLECULE TYPE: protein (iii) HYPOTHETICAL: YES (v) FRAGMENT TYPE: internal fragment (vi) ORIGINAL SOURCE:
        (A) ORGANISM: Escherichia coli
        (B) STRAIN: SV164

(xi) SEQUENCE DESCRIPTION: SEQ ID NO:10:

Asn Ser Thr Ala Leu Phe His Gln Leu Cys Gly Asp Arg Pro Ala Thr
1               5                   10                  15

Leu Leu Leu Glu Ser Ala Asp Ile Asp Ser Lys Asp Asp Leu Glu Ser
                20                  25                  30

(2) INFORMATION FOR SEQ ID NO:11:

(i) SEQUENCE CHARACTERISTICS:
        (A) LENGTH: 32 base pairs
        (B) TYPE: Nucleic acid
        (C) STRANDEDNESS: both
        (D) TOPOLOGY: linear (ii) MOLECULE TYPE: DNA (iii) HYPOTHETICAL: NO (iii) ANTI-SENSE: NO (vi) ORIGINAL SOURCE:
        (A) ORGANISM: DNA fragment synthesized in vitro (xi) SEQUENCE DESCRIPTION: SEQ ID NO:11:

AGCTTATTAC AGCAGACGGG CGCGAATGGA TC                                32

(2) INFORMATION FOR SEQ ID NO:12:

(i) SEQUENCE CHARACTERISTICS:
        (A) LENGTH: 12 base pairs
        (B) TYPE:   Nucleic acid
        (C) STRANDEDNESS: double
        (D) TOPOLOGY: linear (ii) MOLECULE TYPE: DNA (iii) HYPOTHETICAL: NO (iii) ANTI-SENSE: NO (vi) ORIGINAL SOURCE:
        (A) ORGANISM: DNA fragment synthesized in vitro (xi) SEQUENCE DESCRIPTION: SEQ ID NO:12:

TGCTCTAGAG CA                                                     12

(2) INFORMATION FOR SEQ ID NO:13:

(i) SEQUENCE CHARACTERISTICS:
        (A) LENGTH: 1232 base pairs
        (B) TYPE:   Nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Escherichia coli
        (B) STRAIN: B (ix) FEATURE:
        (A) NAME/KEY: CDS
        (B) LOCATION: 1..1233
        (C) IDENTIFICATION METHOD: experimental
        (D) OTHER INFORMATION: /coden_start=1
            /EC_numer=1.1.1.95
            /product= "D-3-Phosphoglycerate-
            dehydrogenase"
            /evidence: EXPERIMENTAL
            /gen= "serA"
            /standard_name= "serA"
            /citation= ([1])

(x) PUBLICATION INFORMATION:
        (A) AUTHORS:     Tobey, K.L.
                         Grant, G.A.
        (B) TITLE: The nucleotide sequence of the
            serA gene of Escherichia coli and
            the amino acid sequence of the
            encoded protein, d-3-phospho-
            glycerate dehydrogenase
        (C) JOURNAL: J. Biol. Chem.
        (D) VOLUME: 261
        (F) PAGES:  12179-12183
        (G) DATE:   1986

(xi) SEQUENCE DESCRIPTION: SEQ ID NO:13:

ATG GCA AAG GTA TCG CTG GAG AAA GAC AAG ATT AAG TTT CTG CTG GTA    48
Met Ala Lys Val Ser Leu Glu Lys Asp Lys Ile Lys Phe Leu Leu Val
1               5                  10                  15

```
GAA GGC GTG CAC CAA AAG GCG CTG GAA AGC CTT CGT GCA GCT GGT TAC      96
Glu Gly Val His Gln Lys Ala Leu Glu Ser Leu Arg Ala Ala Gly Tyr
             20                  25                  30

ACC AAC ATC GAA TTT CAC AAA GGC GCG CTG GAT GAT GAA CAA TTA AAA     144
Thr Asn Ile Glu Phe His Lys Gly Ala Leu Asp Asp Glu Gln Leu Lys
         35                  40                  45

GAA TCC ATC CGC GAT GCC CAC TTC ATC GGC CTG CGA TCC CGT ACC CAT     192
Glu Ser Ile Arg Asp Ala His Phe Ile Gly Leu Arg Ser Arg Thr His
     50                  55                  60

CTG ACT GAA GAC GTG ATC AAC GCC GCA GAA AAA CTG GTC GCT ATT GGC     240
Leu Thr Glu Asp Val Ile Asn Ala Ala Glu Lys Leu Val Ala Ile Gly
 65                  70                  75                  80

TGT TTC TGT ATC GGA ACA AAC CAG GTT GAT CTG GAT GCG GCG GCA AAG     288
Cys Phe Cys Ile Gly Thr Asn Gln Val Asp Leu Asp Ala Ala Ala Lys
                 85                  90                  95

CGC GGG ATC CCG GTA TTT AAC GCA CCG TTC TCA AAT ACG CGC TCT GTT     336
Arg Gly Ile Pro Val Phe Asn Ala Pro Phe Ser Asn Thr Arg Ser Val
            100                 105                 110

GCG GAG CTG GTG ATT GGC GAA CTG CTG CTG CTA TTG CGC GGC GTG CCG     384
Ala Glu Leu Val Ile Gly Glu Leu Leu Leu Leu Leu Arg Gly Val Pro
        115                 120                 125

GAA GCC AAT GCT AAA GCG CAC CGT GGC GTG TGG AAC AAA CTG GCG GCG     432
Glu Ala Asn Ala Lys Ala His Arg Gly Val Trp Asn Lys Leu Ala Ala
    130                 135                 140

GGT TCT TTT GAA GCG CGC GGC AAA AAG CTG GGT ATC ATC GGC TAC GGT     480
Gly Ser Phe Glu Ala Arg Gly Lys Lys Leu Gly Ile Ile Gly Tyr Gly
145                 150                 155                 160

CAT ATT GGT ACG CAA TTG GGC ATT CTG GCT GAA TCG CTG GGA ATG TAT     528
His Ile Gly Thr Gln Leu Gly Ile Leu Ala Glu Ser Leu Gly Met Tyr
                165                 170                 175

GTT TAC TTT TAT GAT ATT GAA AAT AAA CTG CCG CTG GGC AAC GCC ACT     576
Val Tyr Phe Tyr Asp Ile Glu Asn Lys Leu Pro Leu Gly Asn Ala Thr
            180                 185                 190

CAG GTA CAG CAT CTT TCT GAC CTG CTG AAT ATG AGC GAT GTG GTG AGT     624
Gln Val Gln His Leu Ser Asp Leu Leu Asn Met Ser Asp Val Val Ser
        195                 200                 205

CTG CAT GTA CCA GAG AAT CCG TCC ACC AAA AAT ATG ATG GGC GCG AAA     672
Leu His Val Pro Glu Asn Pro Ser Thr Lys Asn Met Met Gly Ala Lys
    210                 215                 220

GAA ATT TCA CTA ATG AAG CCC GGC TCG CTG CTG ATT AAT GCT TCG CGC     720
Glu Ile Ser Leu Met Lys Pro Gly Ser Leu Leu Ile Asn Ala Ser Arg
225                 230                 235                 240

GGT ACT GTG GTG GAT ATT CCG GCG CTG TGT GAT GCG CTG GCG AGC AAA     768
Gly Thr Val Val Asp Ile Pro Ala Leu Cys Asp Ala Leu Ala Ser Lys
                245                 250                 255

CAT CTG GCG GGG GCG GCA ATC GAC GTA TTC CCG ACG GAA CCG GCG ACC     816
His Leu Ala Gly Ala Ala Ile Asp Val Phe Pro Thr Glu Pro Ala Thr
            260                 265                 270

AAT AGC GAT CCA TTT ACC TCT CCG CTG TGT GAA TTC GAC AAC GTC CTT     864
Asn Ser Asp Pro Phe Thr Ser Pro Leu Cys Glu Phe Asp Asn Val Leu
        275                 280                 285

CTG ACG CCA CAC ATT GGC GGT TCG ACT CAG GAA GCG CAG GAG AAT ATC     912
Leu Thr Pro His Ile Gly Gly Ser Thr Gln Glu Ala Gln Glu Asn Ile
    290                 295                 300

GGC CTG GAA GTT GCG GGT AAA TTG ATC AAG TAT TCT GAC AAT GGC TCA     960
Gly Leu Glu Val Ala Gly Lys Leu Ile Lys Tyr Ser Asp Asn Gly Ser
305                 310                 315                 320

ACG CTC TCT GCG GTG AAC TTC CCG GAA GTC TCG CTG CCA CTG CAC GGT    1008
Thr Leu Ser Ala Val Asn Phe Pro Glu Val Ser Leu Pro Leu His Gly
```

```
                          325                 330                 335
GGG CGT CGT CTG ATG CAC ATC CAC GAA AAC CGT CCG GGC GTG CTA ACT      1056
Gly Arg Arg Leu Met His Ile His Glu Asn Arg Pro Gly Val Leu Thr
            340                 345                 350

GCG CTG AAC AAA ATC TTC GCC GAG CAG GGC GTC AAC ATC GCC GCG CAA      1104
Ala Leu Asn Lys Ile Phe Ala Glu Gln Gly Val Asn Ile Ala Ala Gln
            355                 360                 365

TAT CTG CAA ACT TCC GCC CAG ATG GGT TAT GTG GTT ATT GAT ATT GAA      1152
Tyr Leu Gln Thr Ser Ala Gln Met Gly Tyr Val Val Ile Asp Ile Glu
            370                 375                 380

GCC GAC GAA GAC GTT GCC GAA AAA GCG CTG CAG GCA ATG AAA GCT ATT      1200
Ala Asp Glu Asp Val Ala Glu Lys Ala Leu Gln Ala Met Lys Ala Ile
385                 390                 395                 400

CCG GGT ACC ATT CGC GCC CGT CTG CTG TAC TA                           1232
Pro Gly Thr Ile Arg Ala Arg Leu Leu Tyr
            405                 410

(2) INFORMATION FOR SEQ ID NO:14:

(i) SEQUENCE CHARACTERISTICS:
        (A) LENGTH:  410 amino acids
        (B) TYPE:    Amino acid
        (C) STRANDEDNESS: single
        (D) TOPOLOGY: linear (ii) MOLECULE TYPE: protein (xi) SEQUENCE DESCRIPTION: SEQ ID NO:14:

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
            85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
            165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240
```

```
Gly Thr Val Val Asp Ile Pro Ala Leu Cys Asp Ala Leu Ala Ser Lys
            245             250             255
His Leu Ala Gly Ala Ala Ile Asp Val Phe Pro Thr Glu Pro Ala Thr
            260             265             270
Asn Ser Asp Pro Phe Thr Ser Pro Leu Cys Glu Phe Asp Asn Val Leu
        275                 280             285
Leu Thr Pro His Ile Gly Gly Ser Thr Gln Glu Ala Gln Glu Asn Ile
    290             295             300
Gly Leu Glu Val Ala Gly Lys Leu Ile Lys Tyr Ser Asp Asn Gly Ser
305             310             315             320
Thr Leu Ser Ala Val Asn Phe Pro Glu Val Ser Leu Pro Leu His Gly
            325             330             335
Gly Arg Arg Leu Met His Ile His Glu Asn Arg Pro Gly Val Leu Thr
            340             345             350
Ala Leu Asn Lys Ile Phe Ala Glu Gln Gly Val Asn Ile Ala Ala Gln
            355             360             365
Tyr Leu Gln Thr Ser Ala Gln Met Gly Tyr Val Val Ile Asp Ile Glu
    370             375             380
Ala Asp Glu Asp Val Ala Glu Lys Ala Leu Gln Ala Met Lys Ala Ile
385             390             395             400
Pro Gly Thr Ile Arg Ala Arg Leu Leu Tyr
            405             410
```

MICROORGANISMS FOR THE PRODUCTION OF TRYPTOPHAN AND PROCESS FOR THE PREPARATION THEREOF

The invention relates to microorganisms for the production of tryptophan and to a process for the preparation thereof.

It is known that tryptophan metabolism takes place by a single biosynthetic pathway in all micro-organisms hitherto investigated (Somerville, R. L., Herrmann, R. M., 1983, Aminoacids, Biosynthesis and Genetic Regulation, Addison-Wesley Publishing Company, U.S.A.: 301–322 and 351–378; Aida et al., 1986, Bio-technology of amino acid production, progress in industrial microbiology Vol. 24, Elsevier Science Publishers, Amsterdam: 188–206). Tryptophan metabolism, its linkage to serine metabolism, and the genes coding for the principal enzymes are depicted in FIG. 1.

Known processes for tryptophan production are based on the expression of a mutated trpE gene which codes for a tryptophan-insensitive anthranilate synthase together with the other genes of the trp operon on a suitable autonomously replicable vector. Owing to the relatively high copy number of the genes, there is increased expression of the trp genes and correspondingly an increased amount of the individual enzymes of tryptophan metabolism. This results in overproduction of tryptophan.

Examples of such processes are described for a number of organisms: for example for *E. coli*: EP 0 293 207, U.S. Pat. No. 4,371,614, for bacillus U.S. Pat. No. 4,588,687, for corynebacterium and brevibacterium EP 0 338 474. A number of problems of process control arise in these processes. There may be instability and loss of the vector or a slowing of growth of the producer strain.

EP-A-0 401 735 (Applicant: Kyowa Hakko Kogyo Co.) describes a process for the production of L-tryptophan with the aid of corynebacterium or brevibacterium strains which contain recombinant plasmids. These plasmids harbour the genetic information for synthesizing the enzymes DAHP synthase, anthranilate synthase, indole-3-glycerol-P synthase, tryptophan synthase and phosphoglycerate dehydrogenase. Feedback-resistant anthranilate synthase alleles are used.

It is furthermore known to increase tryptophan production in strains with deregulated tryptophan metabolism by introducing a plurality of serA, or serA, B, C, wild-type genes. Thus, Chemical Abstracts CA 111 (1989) 16 86 88q and CA 111 (1989) 16 86 89r describe the use of bacillus strains which overexpress respectively the serA wild-type allele and all wild-type genes of serine metabolism (serA, serB and serC) on plasmids for the production of tryptophan WO-A-87/01130 describes the use of serA, serB and serC wild-type alleles for the production of tryptophan in *E. coli*.

Increasing the tryptophan yield by preventing serine degradation in the cell is disclosed in EP-A-0 149 539 (Applicant: Stauffer Chemical Company). This patent application describes *E. coli* K12 mutants in which the serine-degrading enzyme serine deaminase (sda) is destroyed. It also describes the use of strains of this type for the production of amino acids. Example VIII describes the use of a strain of this type for the overproduction of tryptophan from anthranilate. The explanation for the improved tryptophan yield compared with a strain with intact serine deaminase in the European patent application is that, in microorganisms in which the reserve of tryptophan precursors is very high, serine or the serine biosynthesis capacity is rate-limiting for the production of tryptophan.

The object of the invention was to provide microorganisms which produce increased amounts of tryptophan and to provide processes which make it possible to prepare microorganisms of this type.

The object is achieved by strains of micro-organisms which are characterised in that they have a deregulated tryptophan metabolism and a serine metabolism which is deregulated at least by one feedback-resistant serA allele.

For the purpose of the present invention, feedback-resistant serA alleles means mutants of the serA gene which code for a phosphoglycerate dehydrogenase with a serine sensitivity which is less than that of the corresponding wild-type phosphoglycerate dehydrogenase of the particular microorganism.

The combination according to the invention of at least one feedback-resistant serA allele with a micro-organism with deregulated tryptophan metabolism results in an increase in the tryptophan yield by, astonishingly, up to 2.6-fold compared with the yield achievable with the same microorganism without the feedback-resistant serA allele under culturing conditions which are otherwise the same.

The increased production of tryptophan by the strains according to the invention is unexpected and surprising because feedback-resistant serA alleles show an effect only at a high intracellular serine level (Tosa T, Pizer L. J., 1971, journal of Bacteriology Vol. 106: 972–982; Winicov J., Pizer L. J., 1974, Journal of Biological Chemistry Vol. 249: 1348–1355). According to the state of the art (for example EP-A-0 149 539), however, microorganisms with deregulated tryptophan metabolism have a low serine level. This is why no increase in tryptophan production is to be expected by the introduction, according to the invention, of a feedback-resistant serA allele into microorganisms with deregulated tryptophan metabolism.

BRIEF DESCRIPTION OF THE DRAWINGS

FIG. 3 shows the sequence of the wild-type SerA gene (SEQ ID NO: 13; SEQ ID NO: 14);

FIG. 12 shows the complementing plasmid called pGH5/III; and

FIG. 13 shows the resulting vector pGC3/I which is used to transform *Corynebacterium glutamicum* ATCC21851.

Figure 1:
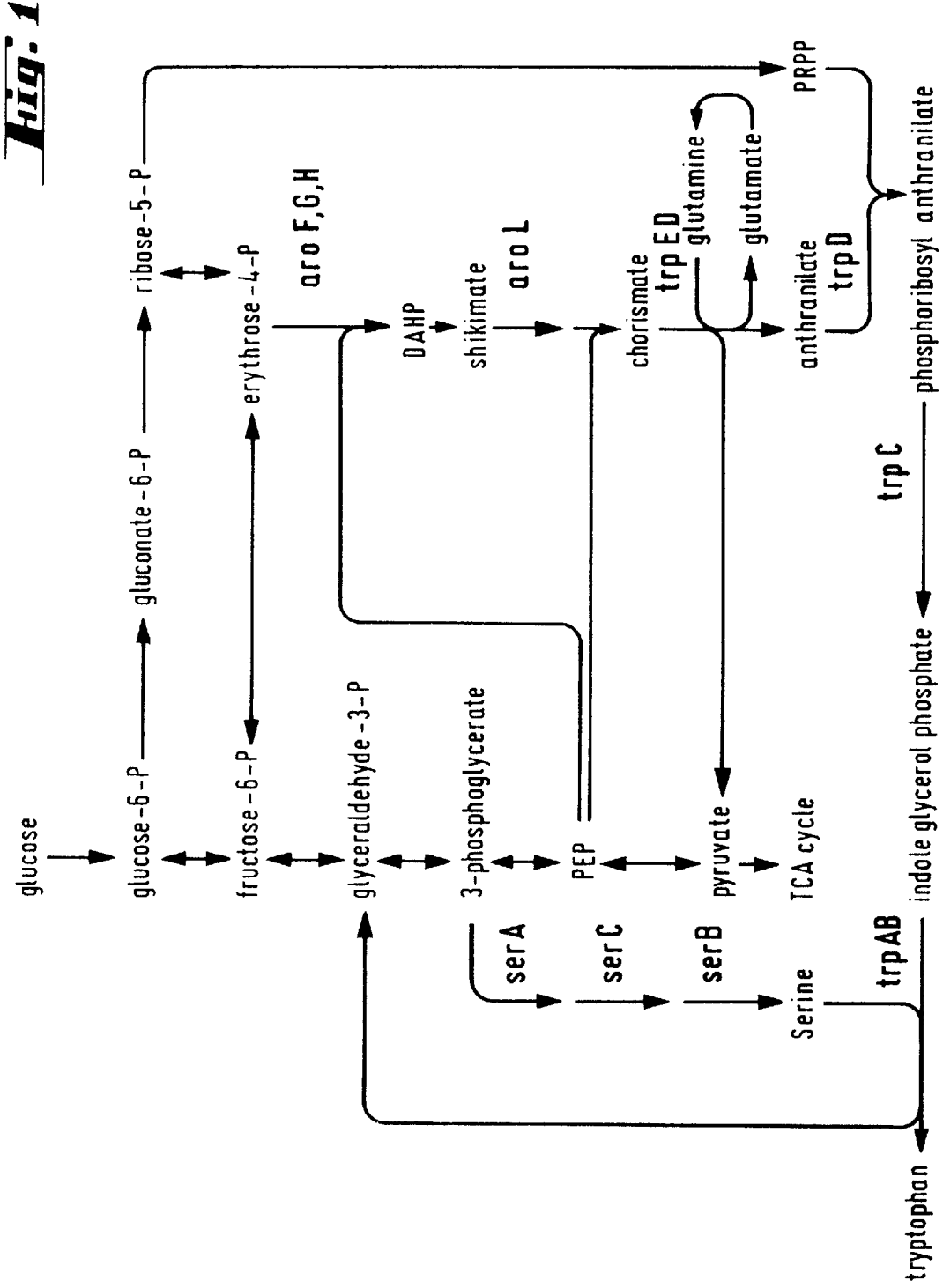
FIG. 1 shows that tryptophan metabolism takes place in all known microorganisms by the depicted metabolic pathway.

Since tryptophan metabolism takes place in all known microorganisms by the metabolic pathway depicted in FIG. 1, and the techniques to be used for preparing the strains according to the invention are known in principle and can be applied to all microorganisms, strains according to the invention can be prepared from any desired microorganisms.

Suitable and preferred for the preparation of a strain according to the invention are bacteria. Gram-negative bacteria, especially *E. coli*, are suitable and particularly preferred.

Strains according to the invention can be obtained by entirely or partially abolishing the regulation of tryptophan metabolism in a desired tryptophan-prototrophic initial strain, and introducing a feedback-resistant serA allele into this strain.

Strains according to the invention can likewise be obtained by restoring the ability to synthesise tryptophan in tryptophan-auxotrophic initial strains, with deregulation of the restored tryptophan metabolism, and introducing a feedback-resistant serA allele into strains of this type.

Deregulation of tryptophan metabolism in microorganisms is possible by a number of different processes which are known from the state of the art.

One possibility for deregulation of tryptophan metabolism is to modify the enzyme anthranilate synthase. This enzyme catalyses the first step in the tryptophan-specific biosynthetic pathway in all microorganisms. Its activity is inhibited by tryptophan, and it thus regulates, depending on the amount of tryptophan, the flow of metabolites through the tryptophan biosynthetic pathway. The enzyme is encoded by the trpE gene.

Mutated trpE genes which code for anthranilate synthases with a tryptophan sensitivity which is less than that of the corresponding wild-type anthranilate synthase, which are also called feedback-resistant trpE alleles hereinafter, can be obtained by mutagenesis and subsequent selection of a tryptophan-prototrophic initial strain. To do this, the relevant strain is subjected to a treatment which induces mutations (Miller J. H., 1972, Experiments in Molecular Genetics, Cold Spring Habor [sic] Laboratory, U.S.A.: 113–185).

The treated strain is cultured on a nutrient medium which contains at least one tryptophan antagonist in an amount sufficient to inhibit growth of the strain. Examples of suitable tryptophan antagonists are 4-methyltryptophan, 5-methyltryptophan, 6-methyltryptophan, halogenated tryptophans, tryptazan, indole and indoleacrylic acid.

Resistant clones are tested for the tryptophan sensitivity of their anthranilate synthase. The tryptophan sensitivity of the anthranilate synthase can be determined by any method which permits the activity of this enzyme to be determined in the presence of tryptophan. For example, chorismate can be reacted in a suitable buffer system with glutamine, which is its partner in the reaction, under enzyme catalysis (Bauerle R. et al., 1987, Methods in Enzymology Vol. 142: 366–386). Aliquots were removed from the assay mixture kinetically, and the amount of the reaction product anthranilate produced per unit time was determined by HPLC analysis. The amount of anthranilate produced per unit time is a direct measure of the activity of anthranilate synthase. The assay is carried out in the presence and absence of tryptophan in order to determine the sensitivity of the anthranilate synthase assayed.

It is equally possible to generate tryptophan-insensitive trpE alleles by direct genetic manipulation (Bauerle R. et al., 1987, Methods in Enzymology Vol. 142: 366–386). A number of mutations in the amino-acid sequence of anthranilate synthase leading to a reduced sensitivity of the enzyme to tryptophan have been described for various organisms. (For example for Salmonella: Caliguiri M G., Bauerle R., 1991, J. of Biol. Chem. Vol. 266: 8328–8335; fur brevibacterium, corynebacterium: Matsui K. et al., 1987, J. Bact. Vol. 169: 5330–5332).

There are known methods which make it possible to introduce a mutation at a specific point in a DNA fragment. Methods of this type are described, inter alia, in the following publications:

Sakar G., Sommerauer S. S., 1990, Bio Techniques 8: 404–407, describe polymerase chain reaction-dependent site-directed mutagenesis;

Ausubel F. M. et al., 1987, Current Protocols in Molecular Biology, Greene Publishing Associates, describes [sic] phage M13-dependent methods;

Smith M., 1985, Ann. Rev. Genet. 19: 423–462, describes other methods.

The DNA fragment which embraces the wild-type trpE gene is recombined on a vector using previously described standard techniques for preparing recombinant DNA. Application of the abovementioned methods to the site-directed mutagenesis results in modification of one or more nucleotides in the DNA sequence so that the amino-acid sequence now encoded by the gene corresponds to the amino-acid sequence of a tryptophan-insensitive anthranilate synthase. The described techniques can be used to introduce into any desired trpE gene one or more mutations which result in the encoded anthranilate synthase having an amino-acid sequence which leads to tryptophan insensitivity.

In addition, the following properties are desirable but not absolutely necessary in the strain according to the invention: a defective tryptophan repressor protein, a defective attenuation control of expression of the trp operon, and a defective tryptophanase. These properties can be obtained in the strain according to the invention most simply by choosing an initial strain which already has one or more of the appropriate properties. The preparation or choice can be carried out by a combination of the selection methods mentioned hereinafter.

The tryptophan repressor protein is a major regulatory protein of tryptophan biosynthesis. Together with tryptophan as aporepressor, this protein represses the expression of the trp operon genes. The protein is encoded by the trpR gene. Tryptophan repressor mutants can be selected, for example, from among mutants which are resistant to tryptophan antagonists such as, for example, 5-methyltryptophan. Examples are described in J. Mol. Biol. 44, 1969, 185–193 or Genetics 52, 1965, 1303–1316.

Besides control by the trpR-encoded protein, the trp operon is additionally subject to attenuation control. A DNA region in front of the first gene of the trp operon is responsible for regulation. Mutations or deletions in this region may lead to deregulation. Mutants of this type can be selected from among mutants which are resistant to tryptophan antagonists such as 5-methyltryptophan. On the other hand, mutations of this type, but especially deletions, can be obtained by site-specific induction of this modification, by methods of site-directed mutagenesis, in the attenuation region of the DNA. It is possible, by the techniques already described of site-specific mutagenesis, to recombine the inactivated attenuator region into the chromosome of the strain according to the invention in place of the natural attenuator region.

The enzyme tryptophanase (tnaA) catalyses the degradation of tryptophan to indole, pyruvate and $NH_3$. It is desirable for this enzyme to be inactive in tryptophan producer strains. Strains deficient in this enzyme can be obtained by subjecting the organisms to a mutagenic treatment, and seeking from among the mutants those which are no longer able to utilise tryptophan as a source of carbon and nitrogen. A detailed example is described in J. Bact. 85, 1965, 680–685. Alternatively, it is equally possible to introduce into the tnaA gene, using the abovementioned techniques, site-specific deletions which result in inactivation.

A number of additional mutations of the initial strain are suitable for bringing about a further increase in tryptophan production. Thus, it is preferable for not only the tryptophan biosynthetic pathway but also the general aromatic amino acid biosynthetic pathway (shikimic acid pathway) to be regulation-insensitive. This is why strains which have a regulation-insensitive dehydroarabinoheptulusonate [sic] synthase and whose tyrosine repressor protein (tyrR) is inactivated by a mutation or deletion are preferred as initial strains for preparing strains according to the invention. Equally preferred are strains whose phenylalanine and tyrosine metabolism is impaired. This ensures that the flux of the precursor molecule chorismate is exclusively in tryptophan. Strains of this type have, for example, mutations or deletions in the pheA and/or tyrA genes.

A number of strains are known to be deregulated in one or more steps of tryptophan biosynthesis or the shikimic acid pathway and to overproduce tryptophan. Examples are Bacillus subtilis FermBP-4, FermP1483 (DE 3123001), Brevibacterium flavum ATCC 21427 (U.S. Pat. No. 3,849, 251), Corynebacterium glutamicum, ATCC 21842-21851 (U.S. Pat. No. 3,594,279, U.S. Pat. No. 3,849,251), Micrococcus luteus ATCC 21102 (U.S. Pat. No. 3,385,762), E. coli ATCC 31743 (CA 1182409). These strains are likewise suitable as initial strains for preparing the strains according to the invention. They show that tryptophan producer strains according to the invention can be obtained in a wide variety of organism groups.

Besides the strains with deregulated tryptophan metabolism, required for the preparation of the strains according to the invention is at least one gene which codes for a phosphoglycerate dehydrogenase whose serine sensitivity is less than that of the corresponding wild-type phosphoglycerate dehydrogenase.

Phosphoglycerate dehydrogenase (PGD) is encoded by the serA gene. The sequence of the wild-type serA gene is known (Tobey K. L., Grant G. A., 1986, J. Bac. Vol. 261, No. 26: 1279–1283). Overexpression of the wild-type serA gene product via a plasmid vector is likewise known (Schuller et al., 1989, J. Biol. Chem. Vol. 264: 2645–2648).

The preparation of feedback-resistant serA alleles using classical genetic methods is described by Tosa T., Pizer L. T., 1971, J. Bac. Vol. 106, No. 3: 972–982. In that case selection took place via the resistance of the mutants to the serine analogue serine hydroxamate. The mutations were not characterised in detail in this publication; the effect of the mutation on metabolism was not investigated.

Feedback-resistant serA alleles can also be obtained, for example, by subjecting a microorganism to mutagenesis. Suitable mutagens are UV light and any chemical mutagens such as, for example, ethyl methane-sulphonate or N-methyl-N'nitro-N-nitrosoguanidine. The dosage and exposure time are determined by conventional methods for the chosen mutagen (Miller J. H., 1972, Experiments in Molecular Genetics, Cold Spring Harbor Laboratory, U.S.A.: 113–143).

Mutagen-treated organism populations are subjected to selection for clones with serA genes which code for serine-insensitive phosphoglycerate dehydrogenases. For example, a mutagen-treated population is incubated on solid growth medium which contains serine hydroxamate in an amount sufficient to inhibit the growth of non-resistant bacteria. Resistant clones are assayed for the serine sensitivity of their phosphoglycerate dehydrogenase. One embodiment of this method is described by way of example by Tosa and Pfizer, 1971, J. Bact. 100, 3: 972–982.

Alleles which code for a serine-insensitive phosphoglycerate dehydrogenase can likewise be generated by genetic engineering techniques.

The region of the PGD which mediates the serine regulation is located in the C-terminal region of the protein. This is why insertions, substitutions or deletions of one or more amino acids are preferably introduced in the C-terminal 25% of the PGD protein, particularly preferably in the 50 C-terminal amino acids of the PGD protein. These result in a reduced sensitivity of the PGD to serine.

Alleles which code for PGDs of this type are obtained by modifying the 3' region, which codes for the said C-terminal regions of the PGD, of the serA gene. To do this, the unmutated serA gene is recombined on a cloning vector by using the techniques known to the person skilled in the art for preparing recombinant DNA, such as restriction, ligation and transformation (Maniatis T., Fritsch E. F. and Sambrook J., Molecular Cloning: A Laboratory Manual 1982, Cold Spring Harbor Laboratory). Specific modifications in the 3' region of the structural gene can be achieved, for example, by techniques of site-directed mutagenesis.

Examples of serine-insensitive PGDs which are suitable for expression in microorganisms with deregulated tryptophan metabolism are listed in Table 1 by depicting their C-terminal amino-acid sequence. Apart from the depicted region, the protein sequences of the enzymes do not differ from the wild-type sequence.

The following assays were used to test the gene products of the serA alleles for PGD activity and serine sensitivity:

The PGD activity was determined by detection of the forward or reverse reaction of the enzyme by the method of McKitrick, J. C. and Lewis J. P., 1980, J. Bact. 141: 235–245. The enzyme activity is measured in this case without serine and with various concentrations of serene. The said assay is suitable for determining the serine sensitivity of any phosphoglycerate dehydrogenase. It is likewise possible to employ any other method for measuring the PGD activity.

The measure used for the serine sensitivity of the enzyme is the $K_i$ value, that is to say the serine concentrations which inhibit the activity of the enzyme by 50%. The $K_i$ values and C-terminal amino-acid sequences of a number of feedback-resistant serA alleles and of the wild-type serA gene (serAWT) are listed in Table 1.

TABLE 1

| C-terminal amino-acid sequences of the mutated SerA alleles | | |
|---|---|---|
| | | $K_i$/mM |
| ser AWT | SEQ ID NO: 1 | 0.02 |
| serA 5 | SEQ ID NO: 2 | 0.2 |
| serA 1508 | SEQ ID NO: 3 | 3.8 |
| serA 11 | SEQ ID NO: 4 | 50 |
| serA 1455 | SEQ ID NO: 5 | 100 |

Suitable and preferred for preparing the strains according to the invention are, surprisingly, serA alleles with a $K_i$ value between 100 μM and 50 mM serine.

It is possible to employ for expression of the PGD proteins in the strain according to the invention any recombinant vector which leads to expression of the serine-insensitive serA alleles. A recombinant vector suitable for preparing the strains according to the invention comprises at least one serA gene which codes for a PGD which has a serine sensitivity which is less than that of the wild type, and a vector portion which is autonomously replicable in the recipient strain.

Examples of vectors which are autonomously replicable in E. coli are listed in Pouwels P. H., Enger-Valk B. E., Brammar W. J. 1985, Cloning Vectors, Elsevier, Amsterdam. Vectors of this type include:

Plasmids with a high copy number such as, for example, pBR322; pUC12,

Plasmids with an intermediate copy number such as, for example, pACYC184,177,

Plasmids with a low copy number such as, for example, pSC101,

Phage vectors such as, for example, M13, λ vectors.

Comparable vectors are described for a large number of bacteria (for example EP 0 401 735 for corynebacteria and brevibacteria or in CA 111 (1989) 168688q).

Suitable and preferred are vectors with an intermediate to low copy number; vectors with a p15A replicon, such as pACYC184 (ATCC37033) or pACYC177 (ATCC37031), are particularly preferred.

A large number of vectors for other bacteria are described in the literature (Pouwels et al., 1985, Cloning Vectors, Elsevier Science Publishers, Amsterdam).

Suitable recombinant vectors can be generated by standard techniques for preparing recombinant DNA. These techniques are described in detail, for example, in Maniatis T., Fritsch E. F. and Sambrook J., 1982, Molecular Cloning: A Laboratory Manual, Cold Spring Harbor Laboratory, U.S.A. or Ausubel F. M. et al., 1987, Current Protocols in Molecular Biology, Greene Publishing Associates, U.S.A.

Preparation of recombinant vectors is possible, for example, by fragmenting, using restriction enzymes, the DNA of a donor organism which has in the chromosome or on a recombinant vector a serA allele which codes for a serine-insensitive PGD. The fragmented DNA is ligated by conventional methods, for example by using the enzyme T4 DNA ligase, into a vector molecule which has likewise been linearised by restriction enzymes. The ligation mixture is used to transform recipient strains with deregulated tryptophan metabolism by known processes, such as calcium chloride shock or electroporation. Vectors which contain the required serA alleles can be obtained in recipient strains, for example, by the abovementioned methods such as selection for antibiotic resistance or complementation of serA mutations.

In another embodiment of the strains according to the invention, the serA alleles are integrated as single copy into the chromosome. This can be achieved, on the one hand, by carrying out the mutagenesis and selection strategies described above directly with a tryptophan-deregulated initial strain. It is also possible, on the other hand, to integrate serA alleles which are present on recombinant vectors into the chromosome of the producer strain. A number of methods for integration of this type are known. Descriptions of these techniques are to be found in the following publications:

Phage Lambda-mediated Integration: Balakrishnan and Backmann, 1988, Gene 67: 97–103; Simons R. W. et al., 1987, Gene 53: 85–89;

recD-dependent gene replacement: Shervell et al., 1987, J. Bact. 141: 235–245;

Other methods: Silhavy et al., 1988, Experiments with Gene Fusions, Cold Spring Harbor Laboratory.

Fermentation of strains according to the invention revealed, completely surprisingly, that strains containing a feedback-resistant serA allele with a $K_i$ value for serine between 100 μM and 50 mM and a deregulated tryptophan metabolism, containing a trpE allele with a $K_i$ value for tryptophan between 0.1 mM and 20 mM, provide the highest yield of tryptophan.

The following examples serve to illustrate the invention further.

EXAMPLE 1

Screening for Feedback-Resistant trpE Alleles and Integration of These Alleles Into the Chromosome The tryptophan analogue 5-methyltryptophan was employed for the search for feedback-resistant trpE alleles. N-Methyl-N'-nitro-N-nitroso-guanidine (NG) was used as mutagenic agent. The initial strain used was E. coli K12 YMC9 ATCC33927. The mutagenesis procedure was based on the data of Miller (Miller J. H., 1972, Experiments in Molecular Genetics. Cold Spring Harbor Laboratory, Cold Spring Harbor, N.Y.: 125–129).

About $2 \times 10^9$ cells of YMC9 in the exponential phase of growth from a culture grown in LB were incubated with 50 μg/ml NG in 4 ml of 0.1 M Na citrate buffer pH 5.5 at 37° C. for 30 min. After two washes with 0.1 M phosphate buffer pH 7.0, 0.1 ml of cells was incubated in LB shaking at 37° C. overnight. Subsequently, 0.1 ml of cells from various dilutions ($10^{-3}$, $10^{-4}$, $10^{-5}$ in 0.9% NaCl) were placed on minimal medium plates containing 100 μg/ml 5-methyltryptophan. Besides 5-methyltryptophan, the minimal medium contained 5 g/l glucose, 5 mg/l vitamin B1, 3 g/l $KH_2PO_4$, 12 g/l $K_2HPO_4$, 0.3 g/l $MGSO_4 \times 7H_2O$, 0.1 g/l NaCl, 5 g/l $(NH_4)_2SO_4$, 14.7 mg/l $CaCl_2 \times 2H_2O$, 2 mg/l $FeSO_4 \times 7H_2O$, 1 g/l $Na_3$ citrate and 15 g/l agar. After 24–48 h at 37° C., 5-methyltryptophan-resistant clones were picked out and plated out on the above plates.

The resulting mutants were characterised by determining the $K_i$ value of the trpE gene product for tryptophan (Bauerle R. et al., 1987, Methods in Enzymology Vol. 142: 366–386). It was possible in this way to divide the mutants into two classes. Class 1 mutants had feedback-resistant anthranilate synthases. Class 2 mutants had enzymes with increased anthranilate synthase activity and with an unchanged $K_i$ value.

For characterisation at the molecular level, the relevant DNA regions of the various mutants were cloned and sequenced. For this purpose, the chromosomal DNA was isolated in each case and cleaved with the restriction enzymes NheI and ClaI in one mixture. Fragments with a size of about 5 kb were isolated and ligated to the NheI/ClaI pBR322 fragment which is 4158 bp in size. The ligation mixture was transformed into a trpE strain of E. coli KB 862 (DSM 7196). Clones which were able to grow on minimal medium without tryptophan were selected. The complementing plasmids all contained a 5 kb NheI/ClaI fragment. Besides the trpE and trpD genes, this 5 kb NheI/ClaI fragment also contains DNA regions upstream from trpE (about 0.8 kb) and downstream from trpD (about 1 kb). Table 2 lists the amino-acid sequence differences and the $K_i$ values of 4 Class 1 mutants. The sequences of the mutants agree in the regions which are not depicted with the wild-type sequence.

TABLE 2

Amino-acid sequences of the mutated trpE alleles

|  |  | Kj/mM |
| --- | --- | --- |
| trpE WT | SEQ ID NO: 6 | 0.01 |
| trpE 0 | SEQ ID NO: 7 | 0.1 |
| trpE 5 | SEQ ID NO: 8 | 3.0 |

TABLE 2-continued

Amino-acid sequences of the mutated trpE alleles

|  |  | Kj/mM |
| --- | --- | --- |
| trpE 6 | SEQ ID NO: 9 | <15 |
| trpE 8 | SEQ ID NO: 10 | 15 |

Sequence analysis of the class 2 mutants showed that mutations were present either in the operator region of the trp promoter or in the DNA region which codes for the trp leader peptide. The mutations called ΔtrpL1 and ΔtrpL2 have a deletion which is 136 bp and 110 bp, respectively in size in the DNA region which codes for the leader peptide. The deletion embraces in the ΔtrpL1 mutation the region from nucleotide position 33 to position 168, and in the ΔtrpL2 mutation the region from nucleotide position 11 to 120 in the sequence stored in the EMBL data bank under AC number V00372.

Figure 2:
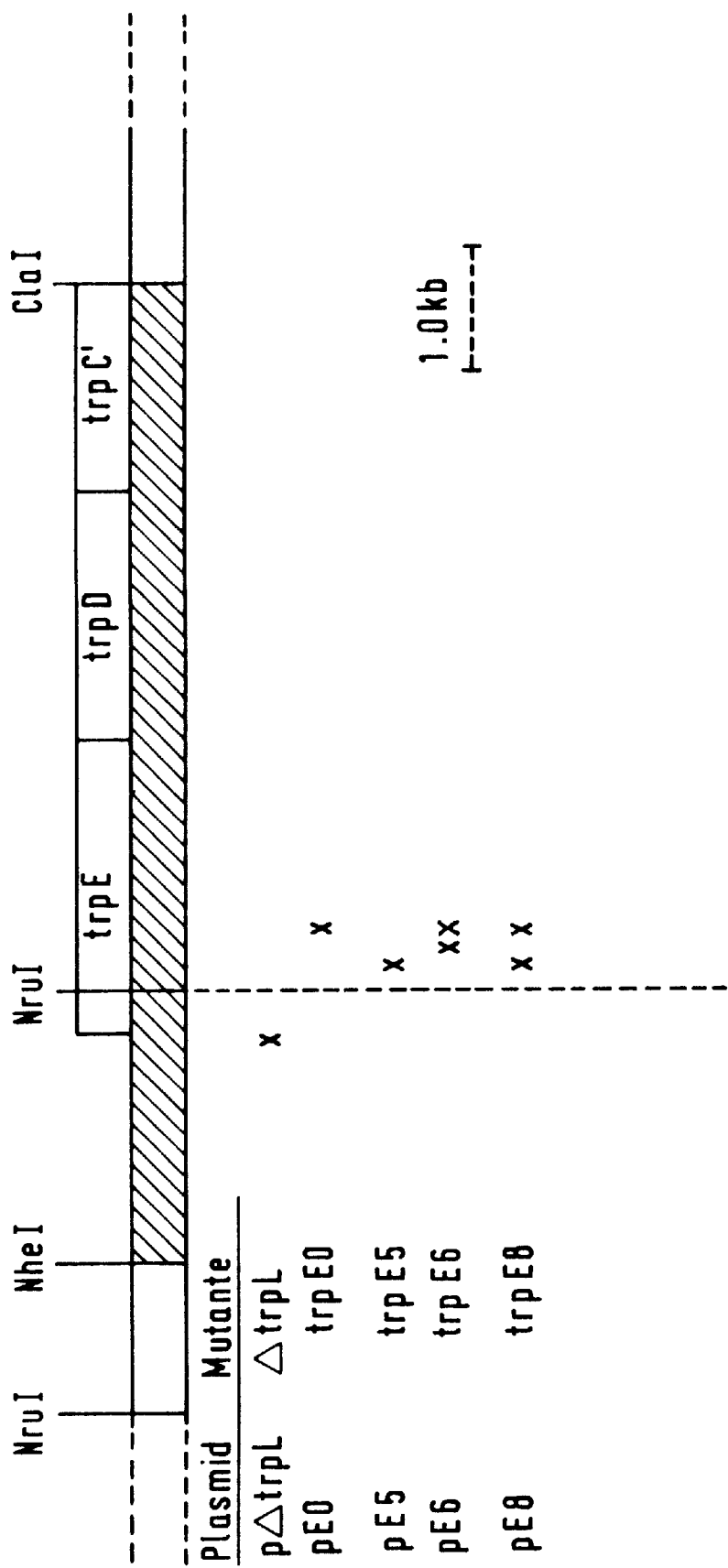
FIG. 2 shows diagrammatically the position of the ΔtrpL1 mutation (class 2) and of the mutations trpE0, trpE5, trpE6 and trpE8 (class 1)

In order to achieve stronger expression of the feedback-resistant trpE alleles, the two mutant classes were combined. The class 2 mutation ΔtrpL1 was used for this. FIG. 2 shows diagrammatically the position of the ΔtrpL1 mutation (class 2) and of the mutations trpE0, trpE5, trpE6 and trpE8 (class 1).

The 1.6 kb NruI fragment which harbours the ΔtrpL1 mutation was isolated from the plasmid pΔtrpL (FIG. 2) and exchanged for the corresponding wild-type NruI fragment of the plasmids pE0, pE5, pE6 and pE8 (FIG. 2). The resulting plasmids were called pIE0, pIE5, pIE6 and pIE8 respectively, and were used for chromosomal integration by homologous recombination. To do this, the chromosomal NheI/ClaI fragment which is about 5 kb in size from each of the said plasmids was isolated from low melting agarose as described in Example 2 and transformed in linear form into the recD strain PD106 [ΔtrpLD102]. The transformation method used was the CaCl$_2$ method of Cohen et al., 1972, Proc. Natl. Acad. Sci. U.S.A. 69: 2110–2114. The strain PD106 was deposited in accordance with the Budapest treaty on 28.07.1992 at the Deutsche Sammlung für Mikroorganismen (DSM) under number 7195 (DSM 7195) the DSM is located at Mascheroder Weg 1B, D-3300 Braunschweig, Germany. Clones which were able to grow on minimal medium without tryptophan and were ampicillin-sensitive, that is to say plasmid-free, were selected. The trpE alleles which code for variously feedback-resistant trpE enzymes and are each combined with the ΔtrpL1 mutation were transferred from the relevant strains into KB862 by P1 transduction (Miller J. H., 1972, Experiments in Molecular Genetics. Cold Spring Harbor, N.Y.: 201–205). The strain KB862 was deposited in accordance with the Budapest treaty on 28.07.1992 at the Deutsche Sammlung für Mikroorganismen (DSM) under number 7196 (DSM 7196). Selection was for growth on tryptophan-free minimal medium. The resulting strains were called PD103 (trpE0), KB862 (trpE5), SV164 (trpE8) and SV163 (trpE6).

EXAMPLE 2

Preparation of serA Genes Which Code for Serine-Insensitive Phosphoglycerate Dhydrogenases [sic].

The serA wild-type gene was cloned from the *E. coli* strain *E. coli* B (ATCC 23226) on the plasmid vector pUC18.

In order to obtain the chromosomal DNA of this strain, it was cultured in Luria broth at 37° C. overnight. The bacterial cells were harvested by centrifugation (4000 g). Lysis of the cells and purification of the DNA were carried out by the protocol described by Ausubel et al., 1987, 2.4.1–2.4.2, Current Protocols in Molecular Biology, Greene Publishing Associates. The amount of DNA obtained was determined by spectrophotometry at a wavelength of 260 nm. The yields were around 600 μg/100 ml.

Figure 4:
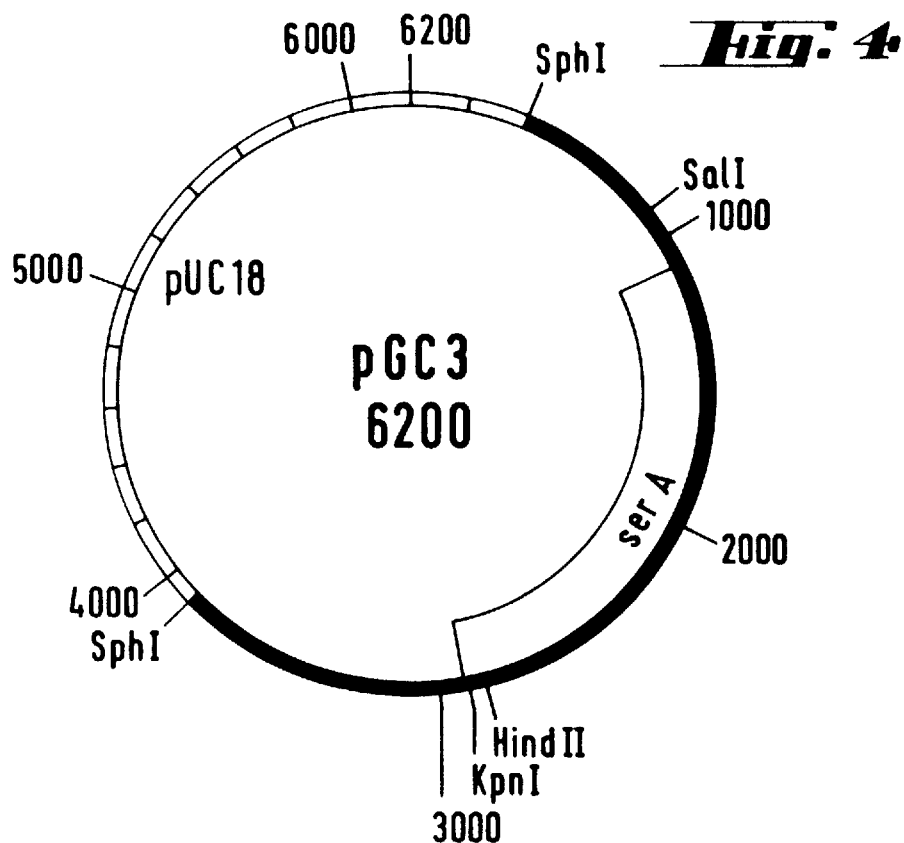
FIG. 4 shows pGC3 which is the recombinant vector with the SerA gene.

10 μg of the chromosomal DNA were cleaved with the restriction enzyme SphI (Boehringer Mannheim GmbH) under the conditions stated by the manufacturer. About 3 μg of the fragment mixture were ligated to 0.2 μg of the autonomously replicable plasmid vector pUC18 (supplied by Boehringer Mannheim GmbH), which had likewise been cut with SphI, by the enzyme T$_4$ ligase (supplied by Boehringer Mannheim GmbH) under the conditions prescribed by the manufacturer. The ligation mixture was used to transform the serA mutant PC1523 (CGSC#:5411;) (CGSC: *E. coli* Genetic Stock Center, Department of Biology 255 OML, Yale University, Postbox 6666, New Haven, Conn., U.S.A.). The transformation method used was the CaCl method of Cohen et al., 1972, Proc. Natl. Acad. Sci . U.S.A. 69: 2110–2114. The transformed bacteria were plated out on minimal medium without serine. Clones which grew without serine contained the serA gene from *E. coli* or an SphI fragment which is 3.5 kb in size. The sequence of the wild-type SerA gene is depicted in FIG. 3 (SEQ ID NO: 13; SEQ ID NO: 14). The recombinant vector with the SerA gene was called pGC3 (FIG. 4).

The serA allele serA5 was prepared by cutting the plasmid pGC3 with the restriction enzymes SalI and KpnI (supplied by Boehringer Mannheim GmbE) in accordance with the manufacture's data. The resulting fragments were fractionated by agarose gelectrophoresis [sic]. The SalI-KpnI fragment which is 2.0 kb in size and which contains the complete serA gene apart from the 8 C-terminal codons was purified from the gel. To do this, the electrophoresis was carried out on low-melting agarose (supplied by Boehringer Mannheim GmbH) so that it was possible to recover the DNA simply by melting the agarose. 0.2 μg of this fragment were ligated with equimolar amounts of a HindIII/SalI-cut pUC18 and of a synthetically prepared, double-stranded oligionucleotide by T$_4$ ligase (supplied by Boehringer Mannheim GmbH) in accordance with the manufacture's data. The nucleotide sequence of this oligonucleotide is as follows.

SEQ ID NO: 11

Figure 5:
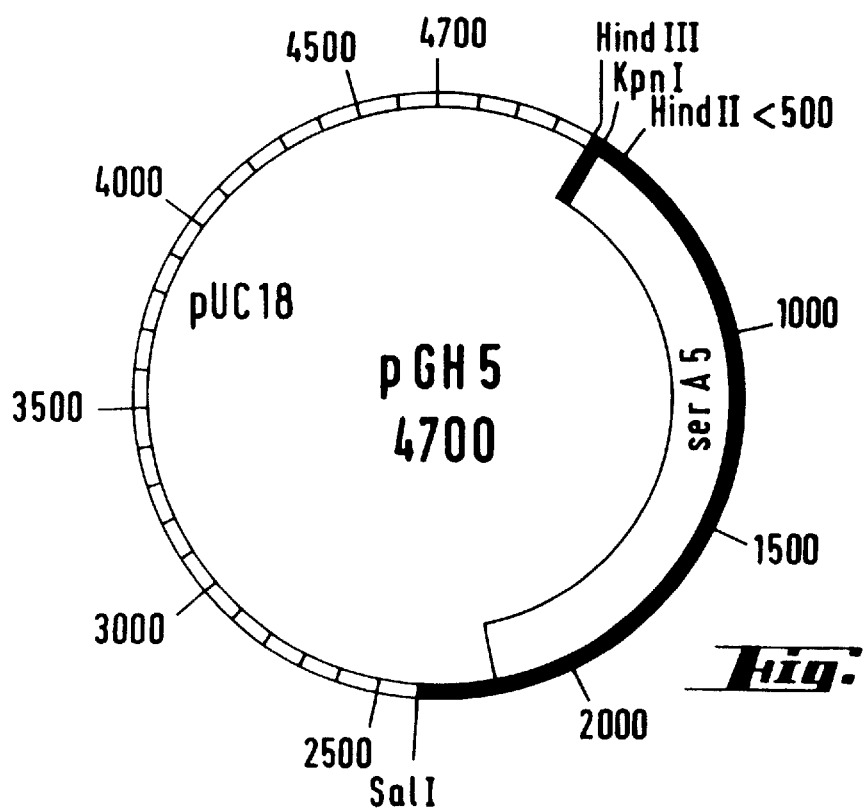
FIG. 5 shows the recombinant plasmid called pGH5.

This oligonucleotide makes up 7 of the 8 last C-terminal codons of the serA gene. The stop triplet TAA is introduced in place of the eighth codon. The phosphoglycerate dehydrogenase encoded by this SerA gene is thus truncated by one C-terminal amino acid. The amino-acid sequence of the mutated PGD is shown in Table 1 (serA5). The recombinant plasmid was called pGH5 (FIG. 5). The serA mutant PC1523 was transformed with the ligation mixture.

Figure 6:
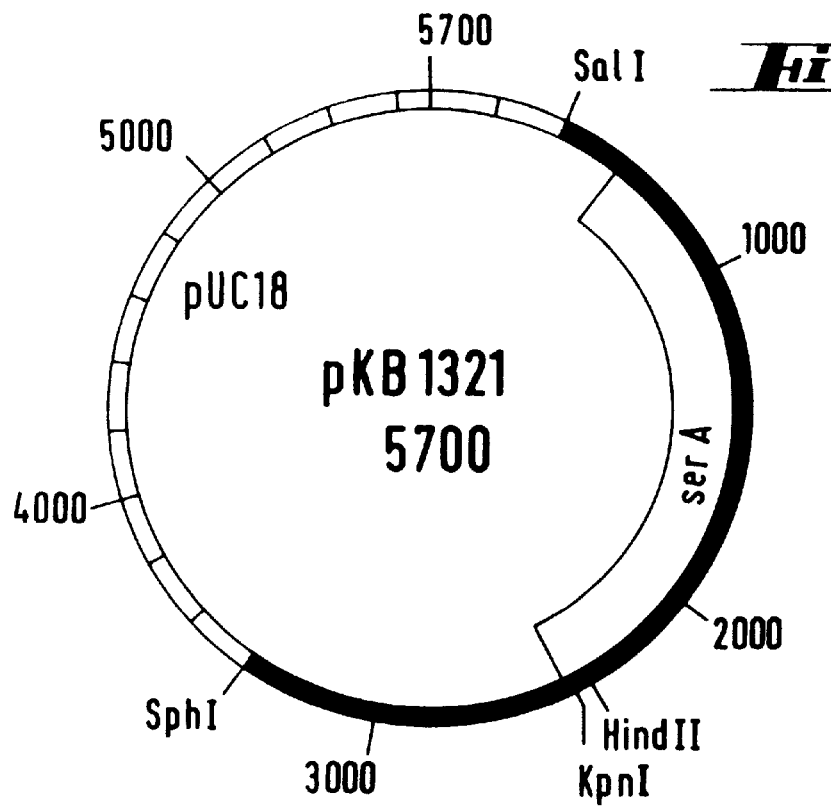
FIG. 6 shows the plasmid called pKB1321.

The serA allele serA1508 was prepared as follows. The plasmid pGC3 was cut with SphI/SalI (supplied by Boehringer Mannheim GmbH) in accordance with the manufacture's data A 3 kb fragment which harbours the complete serA gene was purified by gel electrophoresis and ligated to the SphI/SalI-cut vector pUC18. The resulting plasmid was called pKB1321 (FIG. 6).

pKB1321 was incubated with the restriction endonuclease HindII (supplied by Boehringer Mannheim GmbH) under conditions which permit only partial cutting (0.05 U of enzymes per 1 μg of DNA for 10 min, other reaction conditions in accordance with manufacture's data). This produces, inter alia, a fraction of fragments which is cut by HindII at positions 1793 of the SerA gene. A DNA linker with an XbaI cleavage site was inserted at this point by ligation. The sequence of the DNA linker was as follow:

SEQ ID NO: 12

Figure 7:
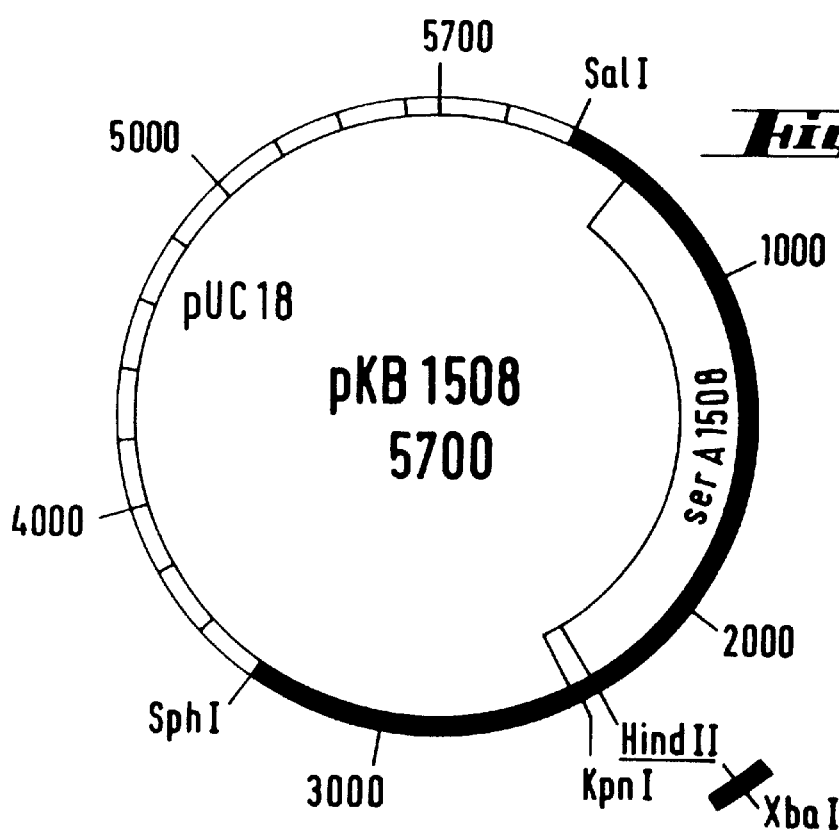
FIG. 7 shows the plasmid called pKB 1508.

Insertion results in a PGD which carries 4 additional amino acids at this point. Its sequence is depicted in Table 1. The plasmid with the insertion was called pKB 1508 (FIG. 7). It was transformed into the serA mutant PC1523.

Figure 8:
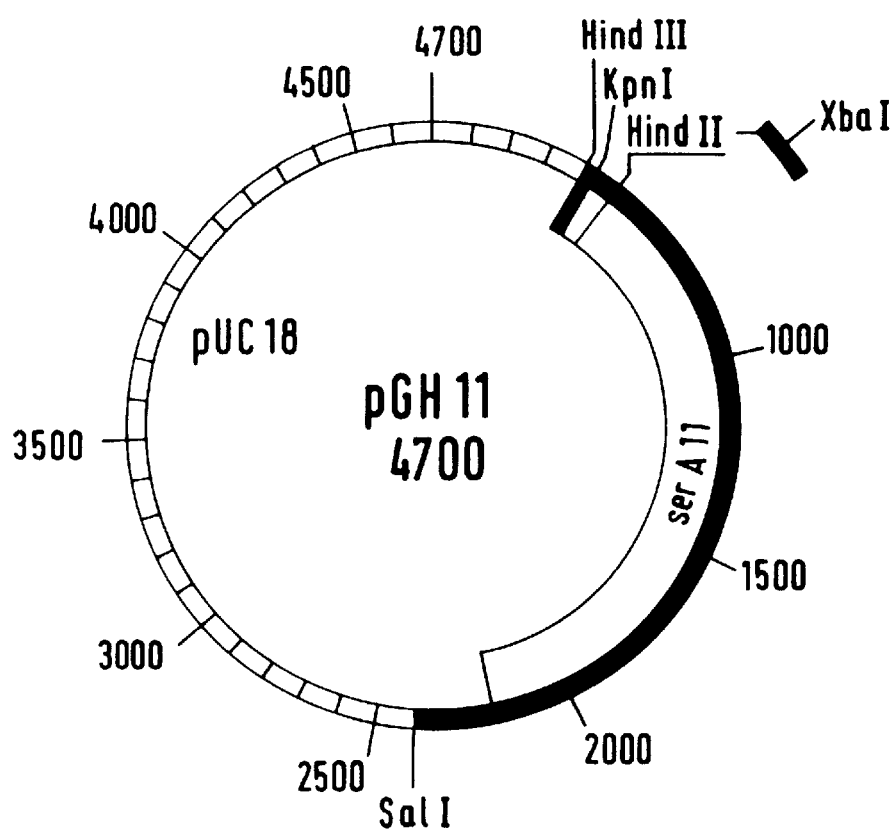
FIG. 8 shows the recombinant plasmid called pGH11.

The serA allele serA11 was prepared by cutting the plasmid pGH5 with SalI and KpnI (supplied by Boehringer Mannheim GmbH) in accordance with the manufacturer's data and purifying the fragment mixture after gel electrophoresis of low-melting agarose. This fragment contains the vector portion from pUC18 and the C-terminal region from serA5. The plasmid pKB 1508 was likewise cut with SalI/KpnI. The DNA fragment which is 2.0 kb in size was eluted from a low-melting agarose gel. This fragment contains the serA allele serA1508 with the insertion mutation, but the 8 C-terminal codons are absent. The two fragments are ligated together and used to transform the serA mutant PC1523. The resulting recombinant plasmid was called pGH11 (FIG. 8). The encoded phosphoglycerate dehydrogenase combines the insertion mutation of serA 1508 with the deletion mutation of serA5. The region with the mutations in the encoded amino-acid sequence is shown in Table 1.

For expression of the mutated serA alleles in producer strains, they were cloned into the vector pACYC 184 (ATCC37033), a vector with an intermediate copy number. To do this, the plasmid pGH5 and the plasmid pGH11 were cut with SalI/HindIII, and the DNA fragments which are each about 2 kb in size and which contain the serA alleles serA5 and serA11 were isolated from low-melting agarose gels. The fragments were treated in separate mixtures with the Klenow fragment of DNA polymerase I from *E. coli* (supplied by Boehringer Mannheim GmbH) in accordance with the manufacturer's instructions in order to convert the 5' protruding cut ends of the restriction enzymes into blunt ends. To do this, 1 µg of each of the fragments was mixed in a 20 µl reaction mixture with 5 U of Klenow enzyme, 0.5 mM dATP, dGTP, dTTP and dCTP and with the buffer recommended by the manufacturer, and incubated at 30° C. for 15 min.

Figure 9:
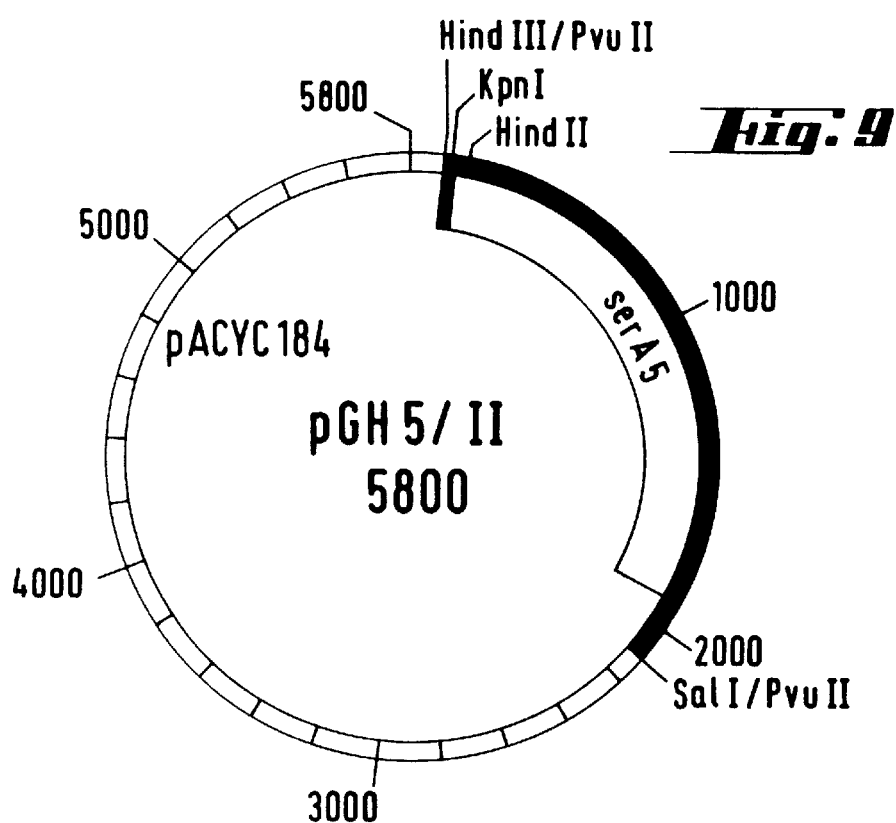
FIG. 9 shows the complementing plasmid called pGH5/II.
Figure 10:
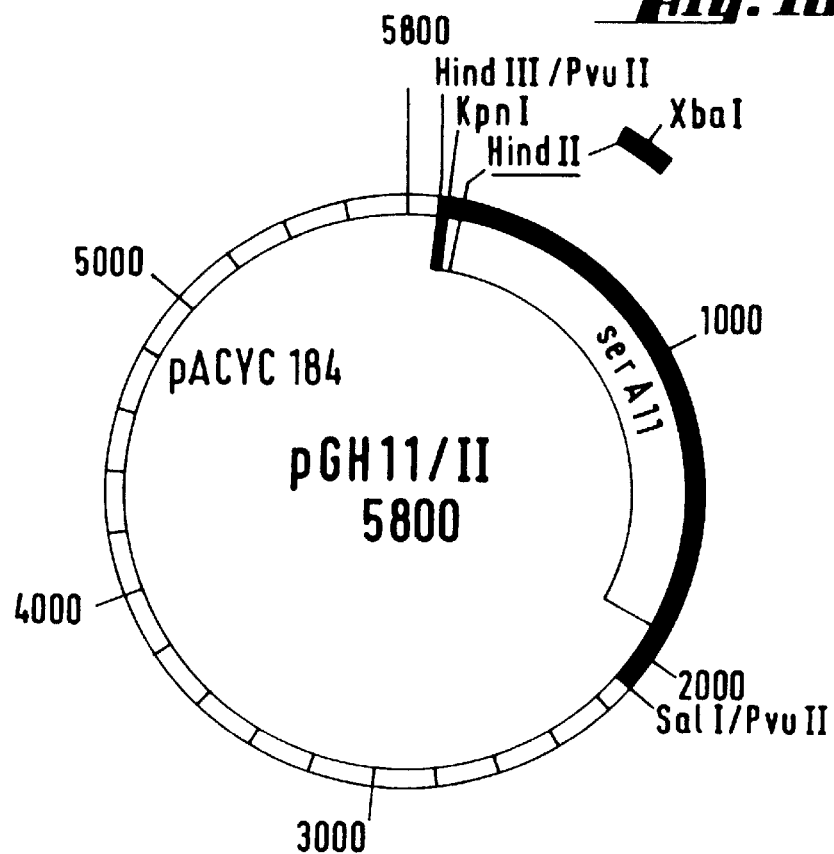
FIG. 10 shows the complementing plasmid called pGH11/II.
Figure 11:
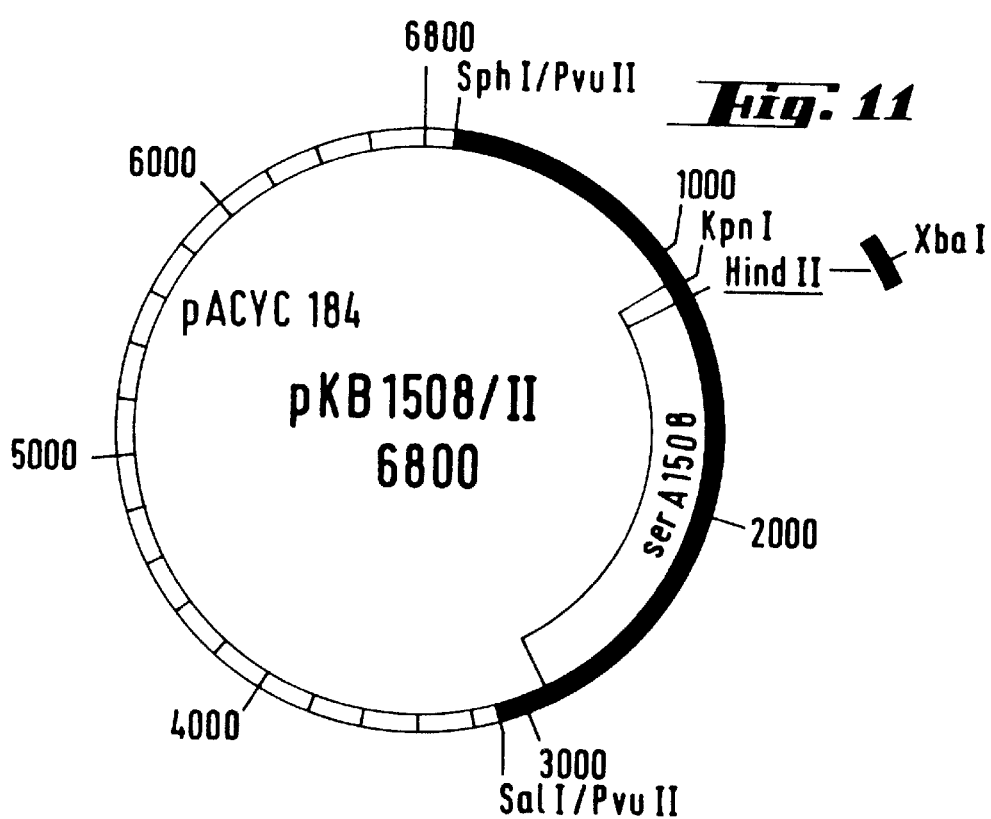
FIG. 11 shows the complementing plasmid called pKB1508/II.

The blunt-ended DNA fragments are [sic] each ligated to a pACYC 184 vector cut with PvuII. The ligation mixtures were used to transform the serA mutant PC1523. Complementing plasmids were called pGH5/II and pGH11/II respectively (FIG. 9, FIG. 10). The plasmid pKB1508 was cut with SalI/SphI. The 3.0 kb fragment which contains the serA allele serA1508 was purified by gel electrophoresis. The fragment was made blunt-ended as described above and was ligated to PvuII-cut pACYC184, and the ligation mixture was transformed into *E. coli* PC1523. Complementing plasmids were called pKB1508/II (FIG. 11).

The plasmids pGH5/II (serA5), pGH11/II (serA11) and pKB1508/II were used to transform the strains PD103 (trpE0), KB862 (trpE5), SV164 (trpE8) and SV163 (trpE6)

EXAMPLE 3

Construction of a Chromosomally Encoded, Feedback-Resistant serA5 Allele Using a Recombinant λ Prophage For integration into the chromosomal lambda attachment site (att λ), the serA5 allele was cloned into the plasmid pRS551 (Simons et al., 1987, Gene 53: 85–96). To do this, the serA5-harbouring HindIII/SalI fragment which is about 2 kb in size was isolated from the plasmid pGH5. The 5' protruding ends were filled in using the Klenow fragment of DNA polymerase I (supplied by Boehringer Mannheim GmbH) in accordance with the manufacturer's data and, after attachment of EcoRI linkers (Maniatis et al., 1982, Molecular Cloning: A Laboratory Manual, Cold Spring Harbor Laboratory, Cold Spring Harbor, N.Y.: 396–397), the 2 kb fragment was ligated into the EcoRI-cleaved vector pRS551. A recombinant plasmid was selected and called pRS5.

By preparing a plate lysate on a pRS5-harbouring recA$^+$ strain (for example YMC9 ATCC33927) with the λRS45 phage, a heterogeneous λ lysate which, besides λRS45 phages, also contained recombinant serA5-harbouring λRS45 derivatives was generated in vivo by homologous recombination (Simons et al., 1987, Gene 53: 85–96).

The serA strain PC1523 (CGSC#:5421) was used to select for recombinant λRS45 derivatives. To do this, PC1523 was infected with the heterogeneous λ lysate (see above) and subsequently plated out on kanamycin-containing. (25 mg/l) LB plates. The resulting lysogenic kanamycin-resistant clones were then tested for their ability to grow on minimal medium plates without serine. A serine-prototrophic clone was selected and used to prepare a homogeneous serA5 λ lysate (by UV induction Simons et al., 1987, Gene 53: 85–96).

This homogeneous serA5 λ lysate was used to infect the tryptophan producer strain SV164. The resulting strain SV164 attλ::serA5 was fermented as described in Example 4. The particular media contained in place of tetracycline as selecting agent in each case 25 mg/l kanamycin.

The tryptophan yields were around 12.5 g/l, compared with 3.5 g/l using the same strain without serA5.

EXAMPLE 4

Tryptophan Production Using Corynebacteria

The plasmid pGH5 is cut with the restriction enzymes SalI and HindIII (supplied by Boehringer Mannheim GmbH), and the DNA fragment which is 2 kb in size and harbours the serA5 gene is isolated from a low-melting agarose gel. The DNA fragment is made blunt-ended by the action of the Klenow fragment of DNA polymerase I from *E. coli* (supplied by Boehringer Mannheim GmbH) as described in Example 2. The vector pWST1 is cut with the restriction enzyme SmaI (supplied by Boehringer) and ligated to the blunt-ended DNA fragment. The vector pWST1 is an *E. coli*/corynebacteria shuttle vector and can replicate both in *E. coli* and in corynebacteria. The corynebacterial replicon of this vector is derived from the strain Corynebacterium glutamicum ATCC 19223. The preparation of the vector pWST1 is described in U.S. Pat. No. 4,965,197. The ligation mixture is used to transform the *E. coli* strain PC1523. Complementing plasmids are called pGH5/III (FIG. 12).

The plasmid pGH5/III is used to transform the tryptophan-producing *Corynebacterium glutamicum* ATCC21851. The transformation is carried out by electrophoration [sic] by the technique described in detail by Wolf H. et al., 1989, Appl. Microbiol. Biotechnol. 30: 283–289. Clones which harbour the recombinant plasmid pGH5/III are selected via the plasmid-encoded kanamycin resistance on agar plates containing 25 mg/l kanamycin.

The plasmid pGC3 is cut with the restriction enzymes SphI and SalI. The 3 kb DNA fragment which harbours the serA wild-type allele is purified and ligated into the vector pWST1 in the manner described above. The resulting vector pGC3/I (FIG. 13) is used to transform Corynebacterium glutamicum ATCC21851.

A Corynebacterium glutamicum ATCC21581 strain which harbours the serA allele 1455 on a plasmid is prepared analogously.

Fermentation reveals that the strain which harbours the serA5 allele on a plasmid achieves the highest tryptophan yields.

EXAMPLE 5

Effect of Various Plasmid-Encoded serA Alleles on the Tryptophan Production of Various trpE Strains 10 ml of LB medium (1% Tryptone, 0.5% yeast extract, 0.5% NaCl), to which 15 mg/l tetracycline were added, in a 100 ml conical flask were inoculated with the various tryptophan producer strains summarised in Table 3. After incubation at 30° C., shaking at 150 rpm, for 8–9 hours, the particular precultures were transferred into 100 ml of SM1 medium. The SM1 medium contained 5 g/l glucose, 3 g/l $KH_2PO_4$, 12 g/l $K_2HPO_4$, 0.1 g/l $(NH_4)_2SO_4$, 0.3 g/l $MgSO_4 \times 7H_2O$, 15 mg/l $CaCl_2 \times 2\ H_2O$, 2 mg/l $FeSO_4 \times 7 H_2O$, 1 g/l $Na_3$ citrate$\times 2H_2O$, 1 ml/l trace element solution (see below), 40 mg/l L-phenylalanine, 40 mg/l L-tyrosine, 5 mg/l vitamin B1 and 15 mg/l tetracycline. The trace element solution was composed of 0.15 g/l $Na_2MoO_4 \times 2H_2O$, 2.5 g/l $H_3BO_3$, 0.7 g/l $CoCl_2 \times 6H_2O$, , 0.25 g/l $CuSO_4 \times 5H_2O$, 1.6 g/l $MnCl_2 \times 4H_2O$ and 0.3 g/l $ZnSO_4 \times 7H_2O$. The cultures were shaken at 150 rpm in 1 l conical flasks at 30° C. for 12–16 h. The $OD_{600}$ after this incubation was between 2 and 4. Further fermentation is [sic] carried out in BIOSTAT®M research fermenters supplied by Braun-Melsungen. A culture vessel with a total volume of 2 liters was used.

The medium contained 17.5 g/l glucose, 5 g/l $(NH_4)_2SO_4$, 0.5 g/l NaCl, 0.3 g/l $MgSO_4 \times 7H_2O$, 15 mg/l $CaCl_2 \times 2H_2O$, 75 mg/l $FeSO_4 \times 7H_2O$, 1 g/l $Na_3$ citrate$\times 2\ H_2O$, 1.5 g/l $KH_2PO_4$, 1 ml trace element solution (see above), 5 mg/l vitamin B1 (thiamine), 0.75 g/l L-phenylalanine, 0.75 g/l L-tyrosine, 2.5 g/l yeast extract (Difco), 2.5 g/l Tryptone (Difco) and 20 mg/l tetracycline.

The glucose concentration in the fermenter was adjusted to 17.5 g/l by pumping in a 700 g/l (w/v) glucose solution (autoclaved). Before inoculation, tetracycline was added to a final concentration of 20 mg/l in the fermentation medium. In addition, the pH was adjusted to 6.7 by pumping in 25% $NH_4OH$ solution.

100 ml of preculture were pumped into the fermentation vessel for inoculation. The initial volume was about 1 l. The cultures were initially stirred at 400 rpm, and compressed air sterilised with a sterilising filter was passed in at 1.5 vvm. The fermentation was carried out at a temperature of 30° C.

The pH was kept at a value of 6.7 by automatic correction with 25% $NH_4OH$. The oxygen saturation in the fermentation broth ought not to fall below 20% at any time during the fermentation. The oxygen saturation was controlled via the stirring speed during the fermentation.

At intervals of two to three hours, the glucose content of the nutrient solution, the optical density and the tryptophan yield were measured. The glucose content was determined enzymatically using a glucose analyser supplied by YSI. The glucose concentration was adjusted to between 5 and 20 g/l by continuous feeding in.

The tryptophan content of the medium after the fermentation was determined by HPLC. The medium was fractionated on a Nucleosil 100-7/C8 [lacuna] (250/4 mm; Macherey-Nagel). The column was operated isocractically at a flow rate of 2 ml/min. The mobile phase used was water/acetonitrile (83/17) to which 0.1 ml of $H_3PO_4$ (85%) was added per liter. Detection was carried out either with a diode array detector or at a fixed wavelength of 215 or 275 nm. The fermentation was stopped after 44–50 h. The amounts of tryptophan produced in this fermentation in g/l after 48 h are summarised in Table 3.

TABLE 3

Tryptophan yields with various serA/trpE combinations

| | serAWT | serA5 | serA1508 | serA11 | serA1455 |
|---|---|---|---|---|---|
| trpE0 | 15.7 | 20.2 | n.d. | n.d. | 6.7 |
| trpE5 | 12.5 | 18.9 | 15.0 | 20.0 | 7.5 |
| trpE6 | 11.6 | 24.1 | 13.8 | 24.0 | 4.0 |
| trpE8 | 7.5 | 18.0 | n.d. | 11.5 | 3.9 | n.d. not determined

What is claimed is:

1. A tryptophan producing strain of microorganism, said tryptophan producing strain of microorganism being selected from the group consisting of *E. coli* and Corynebacteria and is tryptophan feedback resistant and serine feedback resistant and wherein said serine feedback resistance is by a mutation in a serA allele, where the mutated serA allele codes for a protein which has a $K_i$ value for serine between 0.1 mM and 50 mM; and wherein said tryptophan feedback resistance is by a trpE allele which codes for a protein which has a $K_i$ value for tryptophan between 0.1 mM and 20 mM.

2. The strain according to claim 1, wherein the serA allele is integrated into the chromosome.

3. The strain according to claim 1, wherein the bacteria belong to the species *E. coli*.

4. The strain according to claim 1, wherein the bacteria belong to the species Corynebacteria.

5. The strain according to claim 1, wherein the serA allele mutation has a C-terminal amino acid sequence selected from the group consisting of:

(SEQ ID NO:2);
(SEQ ID NO:3);
(SEQ ID NO:4); and
(SEQ ID NO:5).

6. The strain according to claim 1, wherein said trpE allele has an amino acid sequence selected from the group consisting of (SEQ ID NO:7);
(SEQ ID NO:8);
(SEQ ID NO:9); and
(SEQ ID NO:10).

7. The strain according to claim 1, wherein the serA allele mutation has a C-terminal amino acid sequence selected from the group consisting of:

(SEQ ID NO:2);
(SEQ ID NO:3);
(SEQ ID NO:4);
(SEQ ID NO:5); and wherein said trpE allele has an amino acid sequence selected from the group consisting of (SEQ ID NO:7);
(SEQ ID NO:8);
(SEQ ID NO:9); and
(SEQ ID NO:10).

8. Process for the preparation of a tryptophan producing strain of microorganism comprising providing a tryptophan producing strain of microorganism selected from the group consisting of *E. coli* and Corynebacteria with a tryptophan feedback resistance;

introducing a serine feedback-resistance serA allele into said microorganism strain with said tryptophan feedback resistance; and wherein said serine feedback-resistance is by a mutation in a serA allele, where the mutated serA allele codes for a protein which has a $K_i$ value for serine between 0.1 mM and 50 mM; and wherein said tryptophan feedback resistance is by a trpE allele which codes for a protein which has a $K_i$ value for tryptophan between 0.1 mM and 20 mM.

9. Process according to claim 8, comprising introducing the serA allele into the chromosome of the strain of microorganism with said tryptophan feedback resistance.

10. In a method for producing tryptophan comprising culturing a tryptophan producing strain of microorganism in a culture medium; and recovering the produced tryptophan from the culture medium; the improvement which comprises utilizing a tryptophan producing strain of microorganism selected from the group consisting of *E. coli* and Corynebacteria which is tryptophan feedback resistant and serine feedback resistant and wherein said serine feedback resistance is by a mutation in a serA allele, where the mutated serA allele codes for a protein which has a $K_i$ value for serine between 0.1 mM and 50 mM to produce said tryptophan; and wherein said tryptophan feedback resistance is by a trpE allele which codes for a protein which has a $K_i$ value for tryptophan between 0.1 mM and 20 mM.

* * * * *